(12) United States Patent
Schroeder et al.

(10) Patent No.: US 10,183,064 B2
(45) Date of Patent: Jan. 22, 2019

(54) DELIVERY SYSTEM COMPRISING A PROTEOLYTIC ENZYME OR EFFECTOR THEREOF FOR USE IN A METHOD FOR ORAL TREATMENT AND USES THEREOF

(71) Applicant: TECHNION RESEARCH & DEVELOPMENT FOUNDATION LTD., Haifa (IL)

(72) Inventors: Avraham D. Schroeder, Binymina (IL); Assaf Yosef Zinger, Haifa (IL); Avishay Herman, Binyamina (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 15/127,034

(22) PCT Filed: Mar. 19, 2015

(86) PCT No.: PCT/IL2015/050288
§ 371 (c)(1),
(2) Date: Sep. 19, 2016

(87) PCT Pub. No.: WO2015/140802
PCT Pub. Date: Sep. 24, 2015

(65) Prior Publication Data
US 2017/0209551 A1    Jul. 27, 2017

Related U.S. Application Data

(60) Provisional application No. 61/968,010, filed on Mar. 20, 2014.

(51) Int. Cl.
| A61K 38/48 | (2006.01) |
| A61K 9/127 | (2006.01) |
| A61K 9/00 | (2006.01) |
| A61C 7/00 | (2006.01) |
| A61C 19/06 | (2006.01) |

(52) U.S. Cl.
CPC ............ *A61K 38/4886* (2013.01); *A61C 7/00* (2013.01); *A61C 19/063* (2013.01); *A61K 9/0063* (2013.01); *A61K 9/127* (2013.01); *C12Y 304/24007* (2013.01)

(58) Field of Classification Search
None
See application file for complete search history.

(56) References Cited

U.S. PATENT DOCUMENTS

| 8,846,064 B2 | 9/2014 | Martynov et al. | |
| 2002/0061300 A1* | 5/2002 | Gokcen | A61K 38/164 424/94.2 |
| 2005/0186526 A1 | 8/2005 | Stewart | |
| 2006/0115785 A1 | 6/2006 | Li et al. | |
| 2007/0003541 A1* | 1/2007 | Faudoa | A61K 38/4886 424/94.65 |
| 2007/0077289 A1* | 4/2007 | Wang | A61K 9/0014 424/450 |
| 2009/0324698 A1* | 12/2009 | Wagner | A61K 9/0034 424/450 |
| 2010/0021416 A1* | 1/2010 | Lichter | A61K 9/0046 424/78.17 |
| 2012/0195945 A1* | 8/2012 | Martynov | A61K 8/14 424/401 |
| 2013/0164822 A1 | 11/2013 | Protolease | |
| 2015/0050617 A1* | 2/2015 | Marynka Kalmani | A61K 38/48 433/172 |

FOREIGN PATENT DOCUMENTS

| DE | 3719367 A1 | 12/1988 |
| WO | 2004084873 A1 | 10/2004 |
| WO | 2013164822 A1 | 11/2013 |
| WO | 2013164822 A1 | 11/2013 |
| WO | 2013165304 A1 | 11/2013 |
| WO | WO 2013/165304 | * 11/2013 ............. A61K 38/48 |

OTHER PUBLICATIONS

Jena Bioscience, Data sheet for phosphatidylcholine, 2014, one page.*
Gibco, "Collagenase," 2013, 2 pages. (Year: 2013).*
Dennisr . Stewarett Al: "Use of Relaxin in Orthodontics" Annals of The New York Academy of Sciences, vol. 1041, No. I, May 1, 2005 (May 1, 2005), pp. 379-387.
S Kapila et al: "Induction of MMP-1 (collagenase-1) by relaxin in fibrocartilaginous cells requires both the AP-1 and PEA-3 promoter sites" Orthodontics and Craniofacial Research, vol. 12, No. 3, Aug. 1, 2009 (Aug. 1, 2009), pp. 178-186.
Leonaredi et al: "MMP-13(collagenase 3) immunolocalisation during initial orthodontic tooth movement in rats", Acta Histochemica, Elsevier, Amsterdam, NL, vol. 109, No. 3, May 16, 2007 (May 16, 2007), pp. 215-220.

(Continued)

*Primary Examiner* — Brian Gulledge
(74) *Attorney, Agent, or Firm* — The Roy Gross Law Firm, LLC; Roy Gross

(57) ABSTRACT

The present disclosure provides a delivery system comprising (i) a physiologically acceptable carrier and (ii) a proteolytic enzyme or effector thereof for use in a method for relaxing fibers within a subject's oral cavity. In some embodiments, the relaxation is for use in tooth manipulation (particularly repositioning). In some embodiments, the method involves the use of the proteolytic enzyme or effector thereof at a concentration effective to cause relaxation of fibers between the tooth's alveolar bone and gingiva while maintaining integrity of the fibers surrounding the tooth. Also disclosed herein are methods for fiber relaxation and/or repositioning of tooth making use of the proteolytic enzyme or effector thereof.

19 Claims, 14 Drawing Sheets

(56) References Cited

OTHER PUBLICATIONS

PCT International Search Report PCT/IL2015/050288 Search Completed Sep. 21, 2015; Search dated Sep. 30, 2015 4 pages.
PCT Written Opinion PCT/IL2015/050288 6 Pages.
John G. Edwards: "The prevention of relapse in extraction cases", American Journal of Orthodontics, Aug. 1971, pp. 128-141, vol. 60, Issue 2.
Silju Mathew: "Orthodontic Tooth Movement and Changes in Gingival Crevicular Fluid: A Review", Journal of Indian Orthodontic Society, 2004, pp. 101-114, vol. 37.
Koichiro Komatsu: "Mechanical Strength and Viscoelastic Response of the Periodontal Ligament in Relation to Structure", Journal of Dental Biomechanics, Jan. 2010, pp. 1-18.
Koichiro Komatsu et al: "Analysis of contribution of collagen fibre component in viscoelastic behaviour of periodontal ligament using enzyme probe", Journal of Biomechanics, 2007, pp. 2700-2706, vol. 40, No. 12.
Hyun-Soo Whang: "An Histochemical Study on the Effects of Collagenase During the Relapse Period Following Rat's Tooth Movement", Korean Journal of Orthodontics, Mar. 1984, pp. 173-183, vol. 14, Issue 1.
Chou Bing Wu: "Biology of the orthodontic tooth movement—using collagenase 3 (MMP-13, matrix metalloprotease 13) as a working model", International Conference on Dental & Oral Health, Aug. 2013, One page.

\* cited by examiner

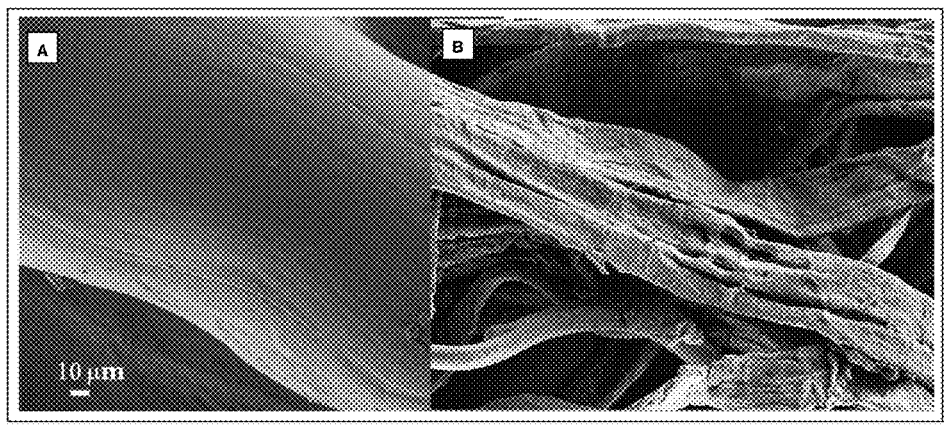
Figure 6A          Figure 6B
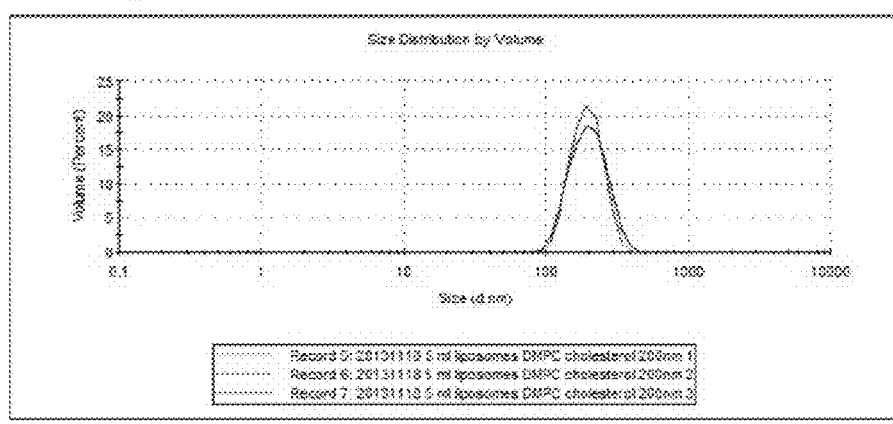
Figure 7

DELIVERY SYSTEM COMPRISING A PROTEOLYTIC ENZYME OR EFFECTOR THEREOF FOR USE IN A METHOD FOR ORAL TREATMENT AND USES THEREOF

This application is a 35 U.S.C. § 371 national phase application of PCT/IL2015/050288, filed Mar. 19, 2015, which claims priority to U.S. 61/968,010 filed on Mar. 20, 2014. Both applications are incorporated herein by reference as if fully set forth.

TECHNOLOGICAL FIELD

The present invention relates to treatment within the oral cavity including dentistry and orthodontics.

BACKGROUND ART

References considered to be relevant as background to the presently disclosed subject matter are listed below:
- US patent application publication No. US2005/0186526
- German patent application publication No. DE3719367
- International patent application publication No. WO2013/164822
- International patent application publication No. WO2013/165304
- International patent application publication No. WO2004/084873

Acknowledgement of the above references herein is not to be inferred as meaning that these are in any way relevant to the patentability of the presently disclosed subject matter.

BACKGROUND

Orthodontic tooth movement demands bone remodeling around the root area.

US2005/0186526 describes methods for accelerating orthodontic tooth movement and for treating relapse by applying force to reposition teeth and administering a tissue remodeling and/or an angiogenic substance to the periodontal tissue surrounding the teeth to be moved.

DE3719367 describes the local administration, in the region of the mandibular joint, of substances influencing the metabolism and/or the structural properties of collagen (such as collagenase-active proteases) in combination with D-penicillamine lathyrogens, glucocorticoids and progestins. The described result is an increased tooth mobility so as to speed up orthodontic correction measures and eliminate occlusal dysbalances. Local administration is able to assist elimination of disturbances of normal functional processes WO2013/164822 describes methods of extracting teeth comprising contacting, prior to extraction, the tissue surrounding a tooth to be extracted with a composition comprising an agent capable of destroying the periodontal ligament surrounding the tooth, such as, collagenase.

WO2013/165304 describes method for modification of mechanical properties or a shape of a mammalian tissue by contacting the tissue with an endopeptidase (referred to as a Tissue-Remodeling Enzymes (TREZ) without causing degradation of the tissue into incohesive parts.

WO2004/084873 describes an oral delivery system for the treatment of periodontal diseases making use of a solid unit dosage form comprising a biodegradable polymer, an antibacterial agent and an anti-inflammatory agent at a defined weight ratio.

GENERAL DESCRIPTION

The present disclosure is based on the development of a technology that involves biological based (blade-free) surgery making use of a proteolytic enzyme being delivered to connective tissue in order to relax the connective tissue (without essentially complete rupture) so as to enable a painless movement of a tooth within the subject's jaw.

Further, the present disclosure is based on the development of liposomal formulations of the proteolytic enzyme being effective to cause relaxation of the connective tissue, at a slow release rate.

Thus, in accordance with its first aspect, there is provided herein a delivery system comprising a physiologically acceptable carrier and a proteolytic enzyme or effector thereof for use in a method for fiber relaxation within a subject's oral cavity.

In some embodiments, the delivery system comprises the proteolytic enzyme or effector thereof at a concentration effective to cause relaxation of fibers between the tooth's alveolar bone and gingiva while maintaining integrity of the fibers surrounding the tooth.

In some embodiments, there is provided herein a delivery system comprising a proteolytic enzyme or effector thereof encapsulated within liposomes, for use in fiber relaxation in the oral cavity.

In some embodiments, delivery system is for cause relaxation of at least fibers between a tooth's alveolar bone and gingival while maintaining integrity of the fibers surrounding said tooth.

In accordance with a second of its aspects, there is provided herein a method for fiber relaxation in a subject's oral cavity comprising administering a delivery system comprising physiologically acceptable carrier and a proteolytic enzyme or effector thereof to said tooth's periodontal pocket. In some embodiments, the concentration of the enzyme delivered to is effective to cause relaxation of between the tooth's alveolar bone and gingival. In some embodiments, the concentration is such that it causes relaxation while maintaining the integrity of the fibers surrounding the tooth.

A further method disclosed in accordance with this aspect of the invention concerns tooth repositioning and comprises administering a delivery system comprising a physiologically acceptable carrier and a proteolytic enzyme or effector thereof to said subject's periodontal pocket at a concentration of said proteolytic enzyme or effector thereof being effective to cause relaxation of fibers between a tooth's alveolar bone and gingival and while said fibers are in relaxed state, repositioning said tooth.

In some embodiments there is provided a method for tooth repositioning comprising administering a delivery system comprising a proteolytic enzyme or effector thereof encapsulated within liposomes to said tooth's periodontal tissue. The concentration of the enzyme upon release from the liposomes being effective to at least cause relaxation of fibers surrounding the tooth, while maintaining the integrity of the fibers between the tooth's alveolar bone and gingival; and while said fibers are in relaxed state, repositioning said tooth.

Finally, there is disclosed herein, according to a further aspect, the use a proteolytic enzyme or effector thereof in the preparation of a delivery system for relaxation of fibers between the tooth's alveolar bone.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 6A and 6B are images showing collagen fibers before (FIG. 6A) and after (FIG. 6B) exposure to free collagenase at the indicated concentrations.

FIG. 7 is a graph showing liposome's size distribution loaded with collagenase.

LIST OF EMBODIMENTS

Figure 1:
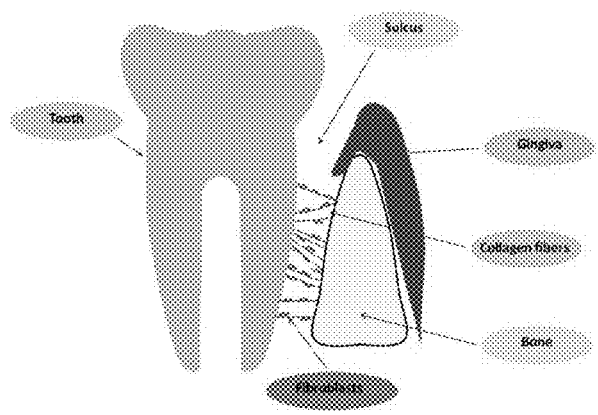
FIG. 1 is a schematic representation of periodontal anatomy.

Some non-limiting embodiments encompassed by the present invention are defined in the following numbered clauses 1. A delivery system for use in a method for relaxing fibers within an oral cavity of a subject, comprising (i) a physiologically acceptable carrier and (ii) a proteolytic enzyme or an effector thereof,
wherein the proteolytic enzyme or effector thereof is at a concentration effective to cause relaxation of at least fibers between a tooth's alveolar bone and gingival.

2. The delivery system of Embodiment 1, wherein said concentration is effective to cause relaxation while maintaining integrity of the fibers surrounding said tooth.

3. The delivery system of Embodiment 1, wherein said proteolytic enzyme is directed to Type I collagen.

4. The delivery system of Embodiment 2, wherein said proteolytic enzyme is collagenase.

5. The delivery system of any one of Embodiments 1 to 4, wherein the concentration of said proteolytic enzyme or said effector thereof is equal to or less than 1 mg/ml.

6. The delivery system of Embodiment 5, wherein the concentration of proteolytic enzyme or said effector thereof is equal to or less than 1.0 mg/ml.

7. The delivery system of Embodiment 6, comprising liposomes encapsulating said proteolytic enzyme or said effector.

8. The delivery system of Embodiment 7, wherein said liposomes are unilamellar or multi-lamellar liposomes.

9. The delivery system of Embodiments 7 or 8, wherein said liposomes comprise at least one liposome forming lipid and cholesterol.

10. The delivery system of any one of Embodiments 7 to 9, wherein said liposomes comprise a mole ratio between said at least one liposome forming lipid and cholesterol of between 50:50 to 95:5.

11. The delivery system of any one of Embodiments 7 to 10, wherein said liposomes comprise a mole ratio between said at least one liposome forming lipid and cholesterol of about 70:30.

12. The delivery system of any one of Embodiments 7 to 11, wherein the liposomes are embedded in a polymeric matrix.

13. The delivery system of any one of Embodiments 1 to 6, comprising a polymeric matrix embedding said proteolytic enzyme.

14. The delivery system of Embodiments 11 or 12, wherein the polymeric matrix comprises a cross-linked polymer.

15. The delivery system of any one of Embodiments 1 to 14 for use in a method for teeth repositioning.

16. The delivery system of any one of Embodiments 1 to 14 for use in a method for orthodontic teeth alignment.

17. A delivery system comprising a proteolytic enzyme or effector thereof being encapsulated within liposomes for use in a method for relaxing fibers within a subject's oral cavity.

18. The delivery system of Embodiment 17, for use in a method for relaxing at least fibers between a tooth's alveolar bone and gingival.

19. The delivery system of Embodiments 17 or 18, wherein said proteolytic enzyme or said effector is encapsulated in the liposomes at a concentration effective to cause relaxation of at least fibers between a tooth's alveolar bone and gingival in said oral cavity.

20. The delivery system of any one of Embodiments 17 to 19, wherein said enzyme is collagenase.

21. The delivery system of Embodiments 17 or 20, wherein said enzyme exhibits a catalytic activity towards Type 1 collagen.

22. The delivery system of any one of Embodiments 17 to 21, wherein said liposomes are mulitlamellar liposomes having an average greater than 1 μm.

23. The delivery system of any one of Embodiments 17 to 21, wherein said liposomes are mulitlamellar liposomes having an average smaller than 1 μm.

24. The delivery system of any one of Embodiments 17 to 23, for use in a method for tooth repositioning.

25. The delivery system of Embodiment 24, wherein said tooth repositioning comprises one or more tooth alignment.

26. A method for causing relaxation of fibers with in a subject's oral cavity, the method comprises administering a delivery system comprising a physiologically acceptable carrier and a proteolytic enzyme or a proteolytic enzyme effector to said subject's periodontal pocket at a concentration of said proteolytic enzyme or effector being effective to cause relaxation of between a tooth's alveolar bone and gingival.

27. A method for tooth repositioning, comprising administering a delivery system comprising a physiologically acceptable carrier and a proteolytic enzyme or effector thereof to said subject's periodontal pocket at a concentration of said proteolytic enzyme or enzyme effector being effective to cause relaxation of fibers between a tooth's alveolar bone and gingival and while said fibers are in relaxed state, repositioning said tooth.

28. The method of Embodiments 26 or 27 wherein said concentration is effective to cause relaxation while maintaining the integrity of the fibers surrounding the tooth.

29. The method of any one of Embodiments 26 to 28, being a non-surgical method.

30. The method of Embodiments 27 or 28, comprising administration of the delivery system in a time interval of up to 12 hours prior to or after applying force onto said tooth.

31. The method of any one of Embodiments 27 to 30, wherein said repositioning of the tooth comprises applying controlled mechanical force onto the tooth.

32. The method of any one of Embodiments 27 to 31, wherein said tooth repositioning comprises tooth alignment.

33. A method for causing relaxation of fibers with in a subject's oral cavity comprising administering to said tooth's periodontal tissue a delivery system comprising (i) a physiologically acceptable carrier and (ii) a proteolytic enzyme or a proteolytic enzyme effector encapsulated within liposomes; at a concentration of said proteolytic enzyme or effector thereof being effective to at least cause relaxation of fibers surrounding the tooth.

34. A method for tooth repositioning comprising administering to said tooth's periodontal tissue a delivery system comprising (i) a physiologically acceptable carrier; (ii) a proteolytic enzyme or effector thereof encapsulated within liposomes at a concentration of said proteolytic enzyme or effector being effective to at least cause relaxation of fibers surrounding the tooth; and while said fibers are in relaxed state, repositioning said tooth.

35. The method of Embodiments 34 or 35, wherein said concentration is such that cause relaxation of fibers while maintaining the integrity of the fibers between the tooth's alveolar bone and gingival.

36. The method of any one of Embodiments 33 to 35, being a non-surgical method.

37. The method of Embodiments 33 or 36, comprising administration of the delivery system in a time interval of up to 12 hours prior to or after repositioning said tooth.

38. The method of any one of Embodiments 34 to 37, wherein said repositioning of the tooth comprises applying controlled mechanical force onto the tooth.

39. The method of any one of Embodiments 34 to 38, wherein said tooth repositioning comprises tooth alignment 40. The method of any one of Embodiments 33 to 39, wherein the delivery system is as defined in any one of Embodiments 1 to 25.

41. Use of a proteolytic enzyme or effector thereof in the preparation of a delivery system for relaxation of fibers between the tooth's alveolar bone and gingival.

42. The use of Embodiment 41, wherein said delivery system comprises liposomes encapsulating said proteolytic enzymes or effector thereof.

DETAILED DESCRIPTION

The present disclosure is aimed at providing a simple, non-surgical, and painless (and even pain-free) solution for various oral procedures, in particular dental procedures that hitherto are either long and elaborating procedures or include a surgical intervention, i.e. including deliberate incision or rupture of biological tissue.

More specifically, the inventors have unexpectedly found that it is sufficient to bring to the tissue to be treated in a subject's supracrestal ligament (comprising at least collagen type I) a low concentration (equal or less than 1 mg/ml) of a proteolytic enzyme, in order to facilitate painless teeth repositioning. The low concentration at the treatment site leads to only relaxation of the tissue connecting the gingival and alveolar bone, without causing complete rupture of the connective tissue surrounding the teeth.

When referring to low concentration at the treatment site it is to be understood to refer to the concentration upon delivery. In some embodiments, the concentration is that of the enzyme when in free form within the site of treatment. In some other embodiments, the concentration is of the enzyme upon release from a delivery device, e.g. from liposomes (which may hold the enzyme in much higher concentration). In yet some other embodiments, the concentration is of the effector that causes an in situ proteolytic enzyme to cause fiber relaxation.

Once the tissue is relaxed it is sufficient to apply minimal mechanical force on the teeth so as to promote it's repositioned without or with less the pain that is typically associated with conventional dental or orthodontic procedures.

Further, the inventors have found that by relaxing the tissue, as opposed to significant rupture, the tissue is capable of completely regenerating and there is no or minimal relapse in the positioning of the tooth.

Based on the above findings, the inventors envisages the use of proteolytic enzymes or effectors thereof, effective on specific connective tissue within the periodontium, to ease dental procedures or other oral cavity medical or cosmetic procedures (less time, less pain, less cost).

Thus, the present disclosure provides, in accordance with its first aspect, a delivery system comprising a proteolytic enzyme or effector thereof for use in a method for fiber relaxation within the oral cavity, wherein the proteolytic enzyme or effector thereof is at a concentration effective, at treatment site, to cause relaxation of fibers between the tooth's alveolar bone and gingiva (alveolar crestal fibers) while maintaining integrity of the fibers surrounding the tooth.

In the following text, when referring to the delivery system it is to be understood as also referring to the methods and uses disclosed herein. Thus, whenever providing a feature with reference to the delivery system, it is to be understood as defining the same feature with respect to the methods or uses, mutatis mutandis.

The delivery systems disclosed herein may be regarded as bio-surgical device or system as it mimics a surgical procedure using biological elements. This bio-surgical system or device manipulates fibers in the tissue so as to cause relaxation of the tissue (regarded herein as the treatment site) to an extent similar to that achieved by surgical cutting with a surgical scalpel.

In some examples, the fibers to be relaxed (namely, the fibers at treatment site) are at least part of the fibers found in the biological width of the gingiva which collectively form the gingival ligament, also known as the supracrestal fibers. Five groups of fiber bundles compose the gingival ligament dentogigival group, alveologingival group, circular group, dentoperiosteal group and transseptal fiber system and in the context of the present disclosure fibers from any of these groups is relaxed following contact with the delivery system comprising the proteolytic enzyme.

Without being bound by theory it is assumed that the low concentration of the proteolytic enzyme or its effector at the tissue site allows to locally reduce fiber tension and or volume (controlled loosening and minimal proteolytic cleavage) in the target connective tissue to thereby relax or release the tension and/or strength of the tissue without significant or complete rupture of the fibers that would involve pain and a long period for tissue regeneration. This tissue tension release can then facilitate various dental procedures that otherwise require surgical cutting of the tissue.

In this connection it is important to note the difference between fiber relaxation and fiber rupture, as done in conventional surgical orthodontic procedures resides in the purpose of the invention disclosed herein. Specifically, by relaxing the fibers rather than surgically cutting it, morbidity, discomfort and pain are reduced as well as orthodontic treatment time and orthodontic treatment side effects (root resorption, poor oral hygiene, poor compliance). In addition, costs of surgically assistant orthodontic treatment and improving significantly the problem of post orthodontic treatment relapse are reduced.

Thus, in the context of the present disclosure fiber relaxation refers to the release of tension and/or strength of the fiber/tissue without significant or complete rupture of the fibers.

In some examples, the delivery system comprises a proteolytic enzyme or its effector for use in a method for tooth repositioning.

In some more specific embodiments, the delivery system is for use in a method for orthodontic tooth repositioning.

In some embodiments, the delivery systems and methods are for treating conditions that involve a fibrotic state. In some embodiments, a fibrotic state involves fibrosis. In some embodiments, the delivery systems and methods are for treating oral submucous fibrosis.

When referring to tooth/teeth repositioning it is to be understood as any procedure that involvements the movement of at least one teeth from its original location/orientation as well as for implanting a teeth (natural or artificial). This may include, inter alia single tooth or some teeth movement for pre prosthodontic or periodontal or endodontical indication), few teeth alignment (such as for post relapse treatment), "six teeth alignment" procedure, and one or two full arches orthodontic treatment. In some embodiments, tooth repositioning includes adjunctive treatment for correction of ankylozsed or traumatized or avulsed teeth, for pre prosthodontic treatment and/or for periodontal treatment. In some embodiments, tooth repositioning refers to orthodontic alignment which can also include implantation of one or more tooth. In some embodiments, tooth repositioning refers to tooth extraction (after sufficient fiber relaxation).

The proteolytic enzyme or effector may be of animal source, microbial source (e.g. *Clostridium histolyticum*) as well as of plant source (papaya—papain). In some embodiments, the proteolytic enzyme is an endogenous enzyme. In some other embodiments, the proteoytic enzyme is an exogenous enzyme.

The enzyme may be naturally occurring, semi synthetic or synthetic enzyme. The naturally occurring, synthetic or semi-synthetic enzymes can be obtained by commonly known laboratory procedures. In some embodiments, the enzyme can be provided by cellular structures, e.g. isolation from bacterial culture.

In some examples, the enzyme is a cysteine protease (also known as thiol proteases) with catalytic mechanism that involves a nucleophilic cysteine thiol. An example of a cysteine protease is papain.

In some examples, the proteolytic enzyme is a metalloprotese, specifically, a zinc protease.

In some examples, the proteolytic enzyme is specific and/or selective to collagen.

When referring to collagen in the context of the present disclosure it is to be understood as including at least one of the five most common types of collagen, namely, collagen Type I; collagen Type II; collagen Type III; collagen Type IV; and collagen Type V.

In some further examples, the proteolytic enzyme is specific and/or selective or affinitive to Type I collagen. By the use of the term "specific to collagen" and more specifically "specific to Type I collagen" it is to be understood that the enzyme has preferential catalytic activity towards Type I collagen over other types of fiber, e.g. over Type III collagen. Thus, in the presence of other fibers the proteolytic enzyme will catalyze the proteolysis of Type I collagen while having no or insignificant catalytic effect on the cleavage of other fibers/polymers.

In some examples, the proteolytic enzyme has absolute specificity to Type I collagen, namely, has neglectable or no detectable catalytic activity to any other fibers.

In one particular example, the enzyme is one that at least catalyzes the proteolytic cleavage of Type I collagen.

In some embodiments, the proteolytic enzyme is collagenase, with catalytic activity with respect to at least Type I collagen.

In some embodiments the enzyme is a collagenase Type II.

In some embodiments the enzyme is a collagenase Type III.

In some embodiments the enzyme is a collagenase Type IV.

In some embodiments the delivery system comprises a proteolytic enzyme effector (also referred to herein as "effector"). In the context disclosed herein a "proteolytic enzyme effector" is a molecule (ion, low molecular weight compound, polymer etc) that affects the in situ level (concentration at target site) of a proteolytic enzyme and/or its activity (at target site). In some embodiments, the effector is an exogenous molecule that increases the level/activity of an endogenous proteolytic enzyme. In some embodiments, such effects affect endogenous pro-collagenase. Examples of effectors on pro-collagenase may include, without being limited thereto, any member belonging to the matrix metalloproteinase (MMP), such as Stromelysin-1, gelatinase, papainase, but also a member of endopeptidase, organomercurials, chaotropic agents, or metal ions like $Zn^{++}$ $Ca^{++}$, $Mg^{++}$, lipooxygenase (LOX) inhibitors.

In some other embodiments, the effector is an exogenous molecule that decreases (inhibits) level/activity of the endogenous proteolytic enzyme.

A list of possible molecules that inhibit proteolytic enzyme activity may include, without being limited thereto, tetracycline, minocycline, doxycycline at subantimicrobial doses, chelating groups such as hydroxamates, carboxylates, thiols, phosphinyls. Also, some may use EDTA, metal ions chelator agents, TIMP (tissue inhibitors of MMP, marimastat and cipemastat which are capable of stopping the collagenase activity without compromising the fibroblasts.

In some other embodiments the protecolytic enzyme effector is a proteolytic enzyme precursor that once in situ (at the target site within the oral cavity) is metabolized to an active proteolytic enzyme.

In some other embodiments, the proteolytic enzyme effector is a molecule that inhibits metabolitic processes/degradation of an endogenous proteolytic enzyme.

The concentration of the proteolytic enzyme or its effector should be sufficient to cause relaxation of the fibers at the supracrestal area but sufficiently low to avoid breakdown of the fibrous bundle connecting the gingival with the alveolar bone.

In some examples, the concentration is less than anyone of 1 mg/ml, 0.9 mg/ml, 0.8 mg/ml, 0.7 mg/ml, 0.6 mg/ml, 0.5 mg/ml, 0.4 mg/ml, 0.3 mg/ml, 0.2 mg/ml, 0.1 mg/ml, 0.09 mg/ml, 0.08 mg/ml, 0.07 mg/ml, 0.06 mg/ml, 0.05 mg/ml, 0.04 mg/ml, 0.03 mg/ml, 0.02 mg/ml, 0.01 mg/ml, 0.009 mg/ml, 0.008 mg/ml, 0.007 mg/ml, 0.006 mg/ml, 0.005 mg/ml, 0.004 mg/ml, 0.003 mg/ml, 0.002 mg/ml.

In some examples, the concentration is at least 0.001 mg/ml, 0.002 mg/ml, 0.003 mg/ml, 0.004 mg/ml, 0.005 mg/ml, 0.006 mg/ml, 0.007 mg/ml, 0.008 mg/ml, 0.009 mg/ml, 0.01 mg/ml, at least 0.025 mg/ml, at least 0.03 mg/ml, 0.04 mg/ml, 0.05 mg/ml, 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml.

In some examples, the concentration is between 0.001 mg/ml to 1.0 mg/ml. In some other embodiments, the concentration is between 0.01 and 0.5 mg/ml. In some other examples, the concentration is between 0.05 mg/ml to 0.25 mg/ml. In some examples, the concentration is between 0.05 mg/ml and 0.1 mg/ml.

In some examples, the proteolytic enzyme or the effector is associated with a physiologically acceptable carrier to form the delivery system.

The term "physiologically acceptable carrier" means a carrier that is useful in preparing a delivery system for the proteolytic enzyme or an effector thereof that is generally safe, non-toxic and neither biologically nor otherwise undesirable, and acceptable for veterinary use as well as human pharmaceutical use.

By the use of the term "associated" or "association" it is to be understood as being carried by the physiologically acceptable carrier by any means of suspension, emulsion, dissolution, embedment, attachment, entrapment, encapsulation, chemical bonding, adsorption, and the like and contemplates any manner by which the proteolytic enzyme or enzyme effector is held to form the integral delivery system.

In some examples, the carrier is a pharmaceutical buffering agent (buffers). Buffers for use in pharmacy are well known in the art and include, inter alia, phosphate buffer solution (PBS), dextrose, etc.

In some examples, the delivery system comprises a matrix, e.g. in which the proteolytic enzyme or the effector is entrapped. In some examples, the matrix is a biodegradable matrix.

In some embodiments, the delivery system comprises an organized collection of lipids, such as liposomes or micelles.

When the delivery system comprises liposomes, it is to be noted that the concentration of the enzyme may be at the higher end of the recited range. In some examples, when the enzyme is associated with liposomes, the concentration thereof can be higher than when in free form and in fact may even reach 1 mg/ml.

In some examples, the delivery system comprises a combination of carriers, such as liposomes or other particulate form within a matrix.

There are various ways to associate the enzyme or the effector as defined herein, either naked or within liposomes or other particulate from, to a matrix. According to one example, a solution or suspension of the enzyme or the effector or of the carrier carrying the enzyme/effector (e.g. liposomes), is mixed with a matrix forming macromolecule in fluid (gelatinous) form. After mixing, the mixture is solidified, by adding a cross linking agent (e.g. $Ca^{2+}$) or by warming up the mixture.

The delivery system may be in the form of a membrane (one or more membranal layers), a lattice, network or network like structure that allows the holding within void(s)/pore(s)/compartment(s), the proteolytic enzyme. The voids' size may vary depending on the matter forming the delivery system and the dimensions of the delivery system, but would typically be of dimensions suitable to prevent, on the one hand, diffusion of the enzyme to other tissues and organs, and on the other hand, to permit a desired flow rate and/or filtering off of the at least one proteolytic enzyme from the biodegradable matrix to the target tissue.

The delivery system (e.g. matrix/liposome) can comprise any biologically degradable or decomposable macromolecule, such as and without being limited thereto, a polymer, a lipid, a polysaccharide, and the like.

In some examples, the biodegradable delivery system comprises one or more interacting polymers to form a polymeric matrix.

In some other examples, the delivery system comprises one or more lipids, interacting together to form an organized collection of lipid (e.g. lipid membrane).

In yet some other examples, the delivery system comprises one or more polysaccharides.

In yet some further examples, the delivery system comprises a combination of one or more of the above macromolecules.

The matter forming the delivery system is also understood to be biocompatible, i.e. has no toxic side effects to the body or is not immunogenic. However, at times, the macromolecules forming the delivery system can have a beneficiary effect, that can promote the procedure for which the enzyme is used. For example, the macromolecule can be of a kind that allows protection of the enzyme or the effector from body harboring enzymes.

In some examples, the delivery system comprise bioerodible macromolecules, the breakdown of which can be a result of any biological or biochemical process including degradation by enzymes, dissolution, hydrolysis etc., to thereby release the embedded enzyme, as will be further discussed below.

In some other examples, the delivery system is formed from or contains lipids, e.g. it comprises a lipid membrane formed into vesicles. There are a variety of lipids that can form into organized collection of lipids (e.g. vesicles, micelles, liposomes and the like). In some examples, the lipid membrane comprises at least glycerophospholipids. The one or more lipids typically disperse in an aqueous media by itself at a temperature above their solid (gel) ordered to liquid disordered phase transition temperature to thereby form a defined three dimensional organized collection of lipids. In some examples, the lipid membrane comprises one or more vesicle forming lipids and more specifically, liposome forming lipids.

The lipids forming the organized collection/vesicles can be the same or different.

In some examples, the delivery system comprises liposomes and the vesicle forming lipids are thus referred to as liposome forming lipids.

In some examples, the proteolyic enzyme is encapsulated within the intraliposomal core of the liposomes.

In some other examples, the proteolytic enzyme is carried by lipid micelles where the enzyme is associated externally to the micelles, e.g. adsorbed to or linked by a linker, e.g. PEG-DSPE. The link of enzymes externally to the carrier can allow the maintaining the enzyme as part of the delivery system while performing the tissue manipulation, namely, without actual, physical release of the enzyme to the tissue to be manipulated. In other words, the enzyme is fixed/anchored onto the delivery system.

In some examples, the enzyme or the effector is loaded into the liposomes (the liposomes being part of the carrier forming the delivery system). This can be achieved by any technique known in the art for loading active agent into liposomes, including, inter alia, active/remote loading, passive loading, dehydration-rehydration techniques.

In some examples, the liposomes are prepared by passive loading. For example, and without being limited thereto, the liposomes forming lipids may be dissolved in an alcohol, e.g. ethanol, or may be warmed (dry) to above their phase transition temperature and then hydrated using an aqueous solution containing the enzyme. The liposomes may then be downsizes to the desired dimensions. For example, the dispersion of liposomes may be extruded through etched membranes with pore diameters of the desired liposome size, e.g. 400, 200 and 100 nm, to form liposomes of the respective defined size.

As also shown in the examples herein, the holding of the enzymes in association with a delivery system such as liposomes or micelles prolong the activity of the enzyme, e.g. by prolonging release rate from the liposomes, into the target connective tissue.

In some examples, the vesicle/lipid forming lipids are glycerophospholipids. As appreciated, the glycerophospholipids have a glycerol backbone wherein at least one, preferably two, of the hydroxyl groups at the head group is substituted by one or two of an acyl, alkyl or alkenyl chain, and the third hydroxyl group is substituted by a phosphate (phosphatidic acid) or a phospho-estar such as phopshocholine group (as exemplified in phosphatidylcholine, PC), being the polar head group of the glycerophospholipid or combination of any of the above, and/or derivatives of same and may contain a chemically reactive group (such as an amine, acid, ester, aldehyde or alcohol).

The lipids may generally be defined by the acyl/alkyl/alkenyl chain length. In some embodiments, the chain(s) are typically between 14 to about 24 carbon atoms in length, and have varying degrees of saturation or being fully saturated, partially or non-hydrogenated.

In some examples, the lipid can be natural, semi-synthetic or fully synthetic lipid, as well as electrically neutral, negatively or positively charged lipid.

In some embodiments, the lipid is a naturally occurring phospholipid.

Examples of lipids forming glycerophospholipids include, without being limited thereto, glycerophospholipid. phosphatidylglycerols (PG) including dimyristoyl phosphatidylglycerol (DMPG); phosphatidylcholine (PC), including egg yolk phosphatidylcholine, dimyristoyl phosphatidylcholine (DMPC), 1-palmitoyl-2-oleoylphosphatidyl choline (POPC), hydrogenated soy phosphatidylcholine (HSPC), distearoylphosphatidylcholine (DSPC); phosphatidic acid (PA), phosphatidylinositol (PI), phosphatidylserine (PS).

Examples of cationic lipids may include, for example, 1,2-dimyristoyl-3-trimethylammonium propane (DMTAP) 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethyl-ammonium bromide (DOME); N-[1-(2,3-dioleyloxy) propyl]-N,N,N-trimethylammonium chloride (DOTMA); 3β[N—(N',N'-dimethylaminoethane) carbamoly] cholesterol (DC-Chol); and dimethyl-dioctadecylammonium (DDAB), N-[2-[[2,5-bis[3-aminopropyl)amino]-1-oxopentyl]amino]ethyl]-N,N-dimethyl-2,3-bis[(1-oxo-9-octadecenyl)oxy]-1-propanaminium (DOSPA), and ceramide carbamoyl spermine (CCS), or the neutral lipid dioleoylphosphatidyl ethanolamine (DOPE) derivatized with polylysine to form a cationic lipopolymer.

In some examples, the vesicle forming lipids are defined by those having a phase transition temperature from solid phase to liquid phase between about 20° C. to 60° C., at times, below 60° C., or below 50° C. or below 40° C. When more than one vesicle forming lipid is used, the total lipids can have together a phase transition temperature from solid phase to liquid phase within the recited range or below the recited upper limit. There are various lipids known in the art to have a phase transition temperature below 60° C.

In some examples, the vesicle forming lipid comprises at least 1,2-dimyristoyl-sn-glycero-3-phosphocholine (DMPC 14:0, 14:0, Mw=677.9, phase transition temperature $T_m$=23.2° C.). In another example, the vesicle forming lipid can comprise 1,2-dipalmitoyl-sn-glycero-3-phosphocholine (DPPC, 16:0, 16:0, Mw=734.1, $T_m$ 41.4° C.) Such lipids are further discussed below. In yet another example the vesicle forming lipid comprises at least hydrogenated soybean phosphatidylcholine (HSPC, 18:0, 16:0 Mw=762.1, $T_m$=52.5° C.).

In some embodiments, the vesicle forming lipids are combined with other lipids, such as a sterol. Without being limited thereto, the sterol is selected from cholesterol, and cholesterol derivatives such as cholesteryl hemisuccinate, cholesteryl sulfate.

Sterols and in particular cholesterol are known to have an effect on the properties of the lipid's organized structure (lipid assembly), and may be used for stabilization, for affecting surface charge, membrane fluidity and/or assist in the loading of the enzyme into the lipid structure (either the matrix or the vesicles).

In some embodiments, a sterol, e.g. cholesterol is employed in order to control fluidity of the lipid structure. The greater the ratio sterol:lipids (the structure forming lipids), the more rigid the lipid structure is.

In some examples, the liposomes comprise a mole ratio between at least one liposome forming lipid and sterol (preferably cholesterol) of between 50:50 to 95:5. In some examples, the liposomes comprise at least 5 mole % cholesterol, at times, at least any one of 10%, 15%, 20%, 25%, 30%, 35%, 40%, 45% or 50%. In some examples the liposomes comprise at most 50 mole % cholesterol, at times, at most any one of 45%, 40%, 35%, 30%, 25%, 20%, 15%, 10%, 5%.

It has been found by the inventors that having at least 20%, but preferably between about 30% to 40% cholesterol in combination with the lipid(s) beneficially delays collagenase release from liposomes.

In some examples, the mole ratio between the liposome forming lipid and the sterol (or cholesterol) is between 60:40 to 80:20. In some examples the mole ratio is about 70:30 (±5%).

When the delivery system comprises liposomes, the liposomes can be any one of multilamellar vesicles (MLVs), multivesicular vesicles (MVVs), small unilamellar vesicles (SUVs), large unilamellar vesicles (LUVs) or large multivesicular vesicles (LMVV). In some embodiments, the liposomes are MLVs. In some other embodiments, the liposomes are unilamellar vesicles.

In some embodiments, the liposomes are characterized by having a size distribution below 1 µm. In some embodiments, the size distribution is between 60 nm to 20 µm. In some other examples, the size distribution is between 100 nm to 600 nm. In some further examples, the size distribution is between 150 nm to 400 nm. In some yet further examples, the size distribution is between 200 nm to 300 nm.

In some examples, the average size of the liposomes is between 120 nm to 300 nm, at times, between 150 nm-250 nm, at times between 180 nm-220 nm, and at times, about 200 nm.

In some embodiments, the liposomes having a size below 1 µm are unilamellar liposomes.

In some other embodiments, the liposomes are characterized by having a size distribution above 1 µm. In some examples, the size distribution is between 1 µm-6 µm. In some further examples, the size distribution is between 1 µm and 5 µm. In some yet further examples, the average size is about 5 µm±0.5 µm.

In some embodiments, the liposomes having a size above 1 µm are multilamellar liposomes.

As appreciated, the biodistribution of the liposomes at the target tissue can be controlled by controlling the liposomes' size. Specifically, liposomes smaller than 1 µm penetrate deep into the tissue. Liposomes having a size greater than 1 µm are retained in the sulcus pocket.

In some examples, the dimensions of the liposomes is determined to correspond with the junctions in the local extracellular matrix (the ECM of the connective tissue) to prevent diffusion of the liposomes to other organs.

In some examples, the delivery system comprises polymeric matrix holding/in association/embedding the enzyme (either within liposomes or in non-liposomal form).

The polymer forming the biodegradable matrix may be non-crossed linked, partially cross-linked or fully cross-linked. In some examples, the matrix comprises cross-linked polymers (fully or partially). The cross linking can be by covalent bonds and/or ionic bonds.

The polymers forming the matrix can be a naturally occurring macromolecule, semi synthetic or synthetic biocompatible and biodegradable macromolecule.

In some examples, the matrix comprises cross-linked polymers to form a water insoluble matrix. The term "water insoluble" is used to denote that upon contact with water or a water containing fluid the cross-linked polymer(s) do not immediately dissolve or disintegrates.

In some examples, the cross-linked matrix is also a water absorbing matrix, to thereby form in an aqueous environment a hydrogel.

As used herein, the term "hydrogel" is used to denote that the polymer, such as a protein or a polysaccharide, once cross linked, is capable of absorbing water in an amount that is at least 4 times, at times 10-50 times and even more of the polymer's own weight thereby forming a gel.

In some examples, the polymeric matrix is in the form of a hydrogel. In some other examples, the polymeric matrix is in solid form and forms into a hydrogel, in situ (upon contact with oral cavity fluids).

In some examples, the polymeric matrix comprises water absorbing cross-linked polymers. Water absorbing cross-linked polymers generally fall into three classes, namely, starch graft copolymers, cross-linked carboxymethylcellulose derivatives, and modified hydrophilic polyacrylates. Examples of such absorbent polymers are hydrolyzed starch-acrylonitrile graft copolymer; a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-cross-linking polyacrylic acid, a cross-linked polyacrylate salt, carboxylated cellulose, and a neutralized cross-linked isobutylene-maleic anhydride copolymer.

In some other examples, the matrix is formed from or comprise synthetic polymers including, without being limited thereto, poly(ethylene oxide) (PEO), poly(vinyl alcohol) (PVA), poly(acrylic acid) (PAA), poly(propylene fumarate-co-ethylene glycol) (P(PF-co-EG)).

In yet some other examples, the polymeric matrix comprises from naturally occurring, hydrogel forming polymers.

In accordance with one example, the matrix comprises at least one hydrogel forming polymer. Without being limited thereto, the polymer is a protein selected from the group consisting of collage, fibrinogen, albumin, alginate, hyaluronate (HA), and gelatin.

In accordance with one further example, the hydrogel forming polymer is a polysaccharide. Non-limiting examples of polysaccharides include agarose, pectin, chitosan, hemicelluloses.

In some examples, the polymeric matrix is a combination of two or more polymers. In accordance with one example, the polymeric matrix comprises a combination of gelatin. For example, gelatin can be combined with chitosan and/or hyaluronan.

In some examples, the polymeric matrix comprises alginate. In some examples, the alginate is a low viscosity (LV) alginate (molecular weight of the polycarbohydrate ~100,000), or very low viscosity (VLV) alginate (molecular weight of the polycarbohydrate ~30,000). The alginate can be cross linked by ions, such as Ca ions to from Ca-alginate cross-linked hydrogel. The cross-linked alginate is a water absorbing polymer, forming in the presence of water a hydrogel. In this connection, it is noted that the inventors have prepared hydrogel from alginate by dissolving 10 mg/ml alginate in water, prepared 0.5-molar Calcium Chloride solution and adding the Alginate solution to the calcium Chloride solution. The size of the drops dictated the size of the gel.

Ionic cross-linked polymers such as cross linked alginate and chitosan normally undergo de-crosslinking and dissolution but can also undergo controlled hydrolysis after partial oxidization.

The rate of dissolution of ionic cross-linked polymers depends on the ionic environment in which the matrix is placed. At times, it is possible to use cross-linked polymer and control the rate of degradation by addition at a desired time and a desired amount of a de-crosslinker, i.e. a substance that interacts with the cross-linker to an extent that the de-cross-linking takes place. For example, a de-crosslinker to Ca in a Ca-alginate cross-linked hydrogel may be de-crosslinked by a di-carboxylic acid such as oxalate (OA).

The enzyme or the effector thereof can also be combined in the delivery system with other pharmaceutically acceptable adjuvants, such as antioxidants, metal ions, such as alkali, alkali earth or transition metals, including, without being limited thereto $Ca^{2+}$, $Mg^{2+}$, $Zn^{2+}$. In one embodiment, the ion is $Ca^{2+}$ which is recognized as a cofactor of collagenase type 1.

The delivery system facilitates delivery of the enzyme/effector to the tissue to be treated. The administration may be directly into the space harboring the fibers, e.g. between the tooth's alveolar bone and gingival or in proximity thereto.

In some examples, the delivery system is used to locally place the enzyme/effector in the periodontal pocket where diffusion of the enzyme/effector to the target tissue to be treated takes place. In some examples, proximity refers to administration such that the matrix has at least one point of physical contact with a portion of the fibers between the tooth's alveolar bone and gingival.

The release of the proteolytic enzyme/effector from the delivery system depends on several parameters, including, without being limited thereto, the type of matrix employed (having specific features such as rate of decomposition, degradation and/or erosion), the concentration of the proteolytic enzyme/effector in the delivery system. At times, concentration equilibrium with the environment dictates the release rate to the connective tissue.

In accordance with some examples, the proteolytic enzyme is released from the delivery system in a controlled manner. Controlled release may be achieved by the particular selection of the matter forming the delivery system. At times, the proteolytic enzyme causes or facilitates the degradation of the biodegradable delivery system e.g. the matrix and thereby being released to its surrounding, namely, to the connective tissue. The release of the enzyme can, at times, be triggered by the concentration of the enzyme at the surrounding of the delivery system, e.g. at the connective tissue to be relaxed.

In some examples, once released, the enzyme (and when an effector is used, the enzyme generated) manipulates the fibers with which it is brought into contact. When referring to manipulation it is to be understood as encompassing at least a relaxation effect, the latter including any one or more of affecting fibers' length (e.g. rupture of a small portion of fibers in a bundle so as to weaken the bundle), strength, shape and uniformity of the bundle of fibers in the connective tissue to which the enzyme is delivered. As stated, the manipulation primarily refers to an effect of relaxing the fibers, causing them to loosen. Fiber relaxing refers to reduction in fiber strength (in Instron) at least 1%, at times, by at least, 2%, 3%, 4%, 5%, 7%, 10% or more as compared to the fiber strength under normal conditions i.e. before manipulation by the enzyme.

The strength of the fiber can be measured by calculating the maximum stress that a fiber can withstand while being stretched or pulled before failing or breaking.

Figures 3A, 3B, 3C:
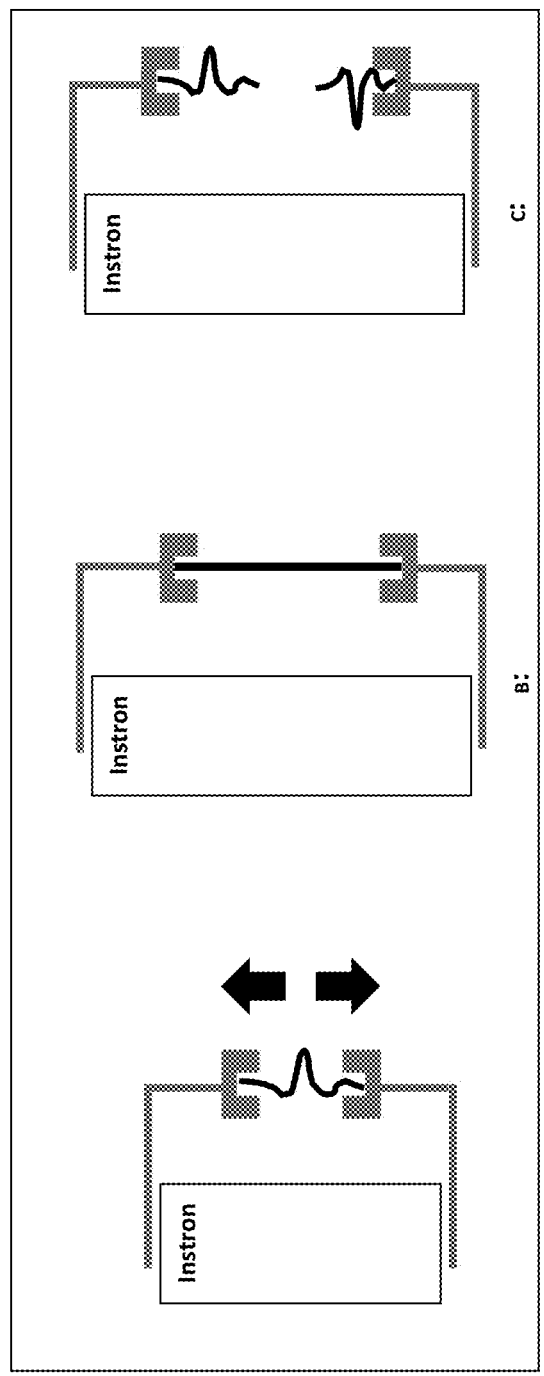
FIGS. 3A-3C are a schematic representation of the experimental setup that was used to test the stress/strength profile of collagen fibers after exposure to collagenase, and was used to test the ability of collagenase to degrade collagen fibers, under relaxed (FIG. 3A) and stressed (FIG. 3B) conditions, and after the tension exceeded the strength of the collagen fiber and the fiber tore (FIG. 3C).

As shown in FIGS. 3A-3C, strength of fibers can be measured by a force machine (Instron) that is used for stressing a fiber bundles. The system stretches each bundle until it is torn in order to measure the tear force that correlated with the mechanical properties.

The delivery system in accordance with the present disclosure is administered with an effective amount of the proteolytic enzyme/effector. The term "effective amount" is intended to mean that amount of the enzyme/effector is sufficient to cause a beneficiary change in the connective tissue without significant damage thereto typically associated with severe rupture of the tissue. For example, a beneficial effect with respect to treatment of periodontal ligaments may be defined as shortening the time and easing the pain necessary for performing corrective tooth alignment when compared to other techniques used for corrective tooth alignment.

The delivery system may be in any physical state suitable to deliver the enzyme/effector to the target connective tissue. To this end, the delivery system may be in fluid or semi fluid state, e.g. as a liquid (physiologically acceptable solution), gel, paste, or as a solid delivery device (e.g. chip, capsule, fiber, cord, disc) When referring to a solid delivery device it can include, for example, a chip, a disc, a film, nanoparticle and/or nanobeads, tubular (thread/wire shape). The delivery system can be in dry form but also applicable as a hydrogel. In some examples, the delivery system can be in the form of a thread or wire. For example, the enzyme can be associated with a medically acceptable suture, e.g. as a coat over the thread or wire or it can be embedded with the matter forming the thread.

The delivery system, when in solid form (i.e. as a delivery device) can have various dimensions, depending on the location and mode of administration. When use as an implant having a three dimensional structure, the delivery device can have at least one dimension being any number in the range of 100 μm to 10 mm, at 200 μm to 7 mm. At times, the device has dimensions that do not exceed 7 mm. in any one of its dimensions. In some examples, the device may have dimensions ranging from any possible combination of dimensions within about $0.1*1*2$ $mm^3$ to about $0.8*3*6$ $mm^3$. In some other examples, the device has dimensions of about $0.5*2*4$ $mm^3$.

The delivery system can be administered to the connective tissue by any acceptable route. In some examples, the delivery system is administered as an implant; in some other examples, the delivery system is administered by injection. In some other examples, the delivery system is administered by inhalation.

Figures 2A, 2B, 2C:
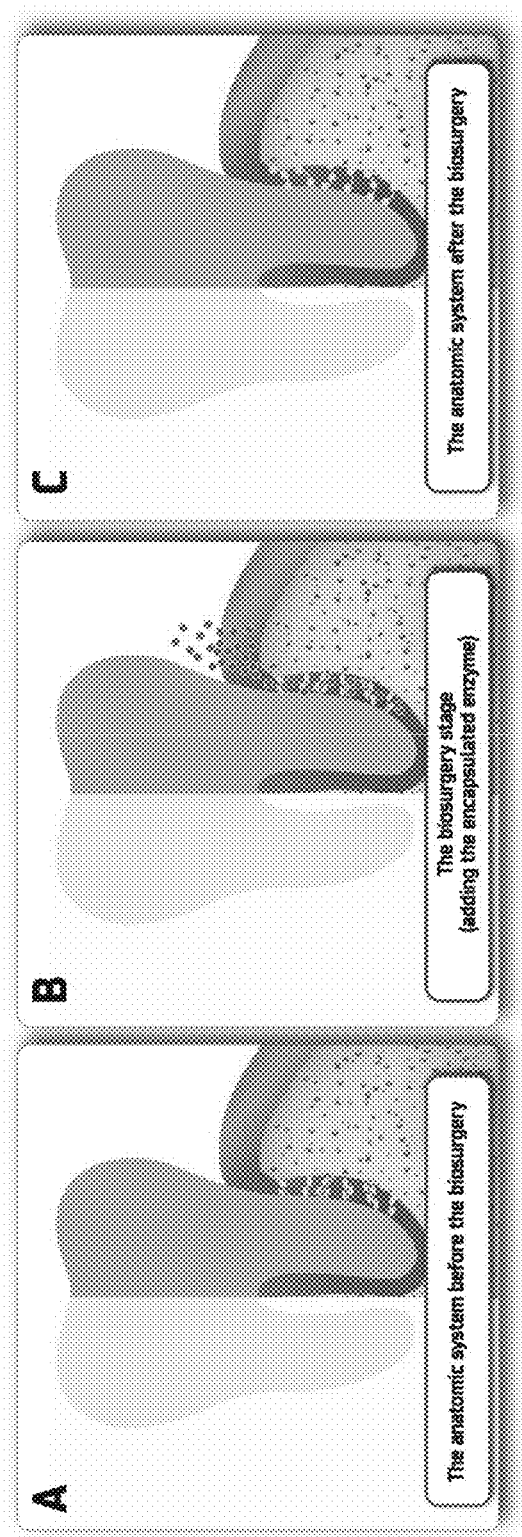
FIGS. 2A-2C are schematic representations of periodontal manipulation before (FIG. 2A), during (FIG. 2B) and after (FIG. 2C) an enzymatic tissue manipulation in accordance with the present disclosure.

In some examples, the delivery system is for manipulating connective tissue in the oral cavity. Specifically, the delivery system can be applicable for manipulating fibrous material of the gingival environment and or the periodontal supporting system. In this connection, FIG. 1 shows a schematic representation of a tooth and the collagen supracrestal fibers connecting the tooth to it's surrounding tissues. In accordance with this example, the delivery system, in the form of particles carrying the enzyme is placed in the supracrestal ligament area and releases the enzyme, in this case, collagenase into the ligament environment to cause loosening of the teeth held to the bone. This is clearly shown by the steps of FIGS. 2(A)-2(C), referred to as the procedure. Specifically, FIG. 2(A) shows that the illustrated tooth is connected to the bone by the illustrated collagen fibers. FIG. 2(B) show the addition of the delivery system, in this example illustrated as particulate matter carrying the proteolytic enzyme; and FIG. 2(C) shows the result of said administration, whereby the proteolytic enzyme caused relaxation of the fibers and release of the tension that holds the tooth to it's surrounding tissues. By that, initiating biological cascade that leads from stress relaxation of the connective tissue (rather than surgically cutting it) to facilitating periodontal tissue (like crestal bone and periodontal ligament and supra crestal fibers) turn over, allowing fastening the orthodontic treatment while reducing morbitity and side effect as mentioned earlier.

Delivery of the enzyme to the supracrestal ligament area may be applicable for various orthodontic or periodontal procedures that require ligament or tension relief. In accordance with some examples, the condition may be removal of tooth, such as a wisdom tooth, tooth alignment and orthodontic corrective treatments. These procedures are known to be long and painful, and may last up to two years or more. The delivery system of the present disclosure can also replace surgical alignment where the connective tissue is deliberately cut. The present disclosure thus provides a non-surgical method, or a surgical method that uses the enzyme or an enzyme effector instead of a blade or other mechanical cutting device. In some embodiments, the method is regarded as a blade-free surgical method.

In line with the above example, there is thus also provided a method of performing a procedure within the oral cavity which involves or requires fiber relaxation (in the jaw), the method comprising administering to the oral cavity, and in particular to the supracrestal are of the periodontal ligament (or in proximity thereto) the delivery system disclosed herein, so as to allow release of the proteolytic enzyme or an enzyme effector, as defined herein, to the ligament.

Specifically, there is provided a method for repositioning of a subject's tooth comprising administering a delivery system comprising proteolytic enzyme or an effector thereof said tooth's periodontal pocket at a concentration of said proteolytic enzyme/effector being effective to cause relaxation of fibers between the tooth's alveolar bone and gingiva while maintaining integrity of the fibers surrounding the tooth, and while said fibers are in relaxed state, aligning said tooth.

Tooth repositioning may be for any purpose known in the art, including tooth alignment, reducing luxative/intusive/ intrusive tooth or teeth to its original site after trauma, like gently extracting a tooth or tooth germ or tooth with a developing root for auto transplantation, like adjunctive technique for releasing ankylosed tooth. In some embodiments, tooth repositioning also encompasses tooth implant, such as implantation of avulsed teeth and auto-transplanted tooth.

In some embodiments, the tooth repositioning is tooth alignment. In some specific embodiments, the tooth repositioning is within the framework of an orthodontic treatment.

In accordance with some other embodiments, the delivery system can be administered in a non-surgical (blade-free) procedure, i.e. a procedure that does not require or involve deliberate cutting of the tissue with scalpel.

The delivery system may be administered once or several times during the dental procedure. In this connection and in accordance with some embodiments, it is to be understood that when referring to a dental procedure, it refers to any procedure involving tooth movement or placement (implantation), replacement. In some embodiments, the dental procedure is an orthodontic procedure. In some other embodiments, the dental procedure is a periodontal procedure. In yet some other embodiments, the dental procedure involves implantation e.g. of avulsed teeth and auto-transplanted tooth.

In accordance with some other embodiments, when referring to dental procedure it is to be understood as referring to a procedure that involves treatment of a fibrotic condition, i.e. where there is excessive fiber formation, in particular in oral sub-mucus area.

In some examples, the administration of the delivery system in a time interval of up to 12 hours, at times, up to 10 hours, at times up to 7 hours, at times up to 5 hours, at times up to 4 hours, at times up to 3 hours, at times up to 2 hours, at times up to 1 hours, before or after applying force on the tooth to be repositioned. The force is a controlled mechanical force in a manner known to those skilled in the art. The delivery system disclosed herein can be administered according to any required regimen. In some embodiments, the delivery system is administered once before or after applying force on the tooth. In some other embodiments, the delivery system is administered several times during a treatment protocol, e.g. during an orthodontic treatment.

Finally, there is disclosed herein the use of a proteolytic enzyme or its effector in the preparation of a delivery system for relaxation of alveolar crestal fibers (between the tooth's alveolar bone and gingival) while maintaining integrity of fibers surrounding the tooth.

NON-LIMITING EXAMPLES

Experimental

All animal trials were approved by the Technion Institutional Ethical Committee (IL-0380313). All animal studies follow strict guidelines as defined by the Max Plank Institutes.

Example 1: Collagen Fibers Treated with Collagenase

Example 1A: The Stress/Strength Profile of Collagen Fibers after Exposure to Collagenase An experimental setup simulating the physiological conditions in the oral cavity consisted of collagen type I bundles sourced from the tails of Wistar rats, suspended using a Lloyd LF-Plus Digital Material Tester (Instron) force machine, inside a bath loaded with a buffer that simulates the delivery system of the oral fluid: 99% water, isotonic solution, pH 6-7 and of variety of electrolytes including sodium, potassium, calcium, magnesium, bicarbonate, and phosphates, collagenase type I from *Clostridium histolyticum* (Sigma-Aldrich) which was added.

The stress/strength profile of the collagen fibers as a function of the collagenase treatment was recorded.

An experimental setup simulating the physiological conditions in the oral cavity consisted of collagen type I bundles sourced from tails of wister rats by sectioning the tail immediately after sacrificing the rat, and removing collagen fibers using surgical tweezers. The rats were sacrificed and the fibers were immediately placed in DMEM growth media comprising glutamine and penicillin. Stress experiments were conducted no more than 72 hr post scarification.

For stress experiments, collagen type I bundles were suspended using a Lloyd LF-Plus Digital Material Tester (Instron) force machine inside a bath loaded with a buffer comprising 99% water, isotonic solution, pH 6-7 and electrolytes including sodium, potassium, calcium, magnesium, bicarbonate, and phosphates. Collagenase type I from *Clostridium histolyticum* (Sigma-Aldrich) was added.

The buffer used in this study simulated the composition of the oral fluid and the experimental setup can be considered as simulating the physiological conditions in the oral cavity.

As shown in FIG. 3, the experimental set up of the system included a force machine (Instron) for stressing the fiber bundles of collagen type I. The system stretched each bundle until it was torn in order to measure the tear force. The tear force correlates with the bundle mechanical properties.

The stress/strength profile of the collagen fibers as a function of collagenase treatment (addition) was then recorded.

Example 1B: Collagenase Relaxes Collagen Fibers

The effect of collagenase on collagen fiber strength was tested at four concentrations: 0.05 mg/ml, 0.1 mg/ml, 0.5 mg/ml, 1 mg/ml, using the step up described with respect to FIG. 3.

Each bundle of fibers was cut in half, the untreated half served as control and the second half was a treated bundle. Both halves were held under similar conditions.

A non-dimensional number was used in order to describe the strength of each fiber:

$$\alpha = \frac{\text{Maximal tearing force of the treated collagen fiber}}{\text{Maximal tearing force of the untreated collagen fiber}}$$

When α equals 1 the mechanical strength of the treated and untreated fibers is equal and when α equals 0 the treated collagen fiber losses its strength and tears, due to collagenase activity.

Figure 4:
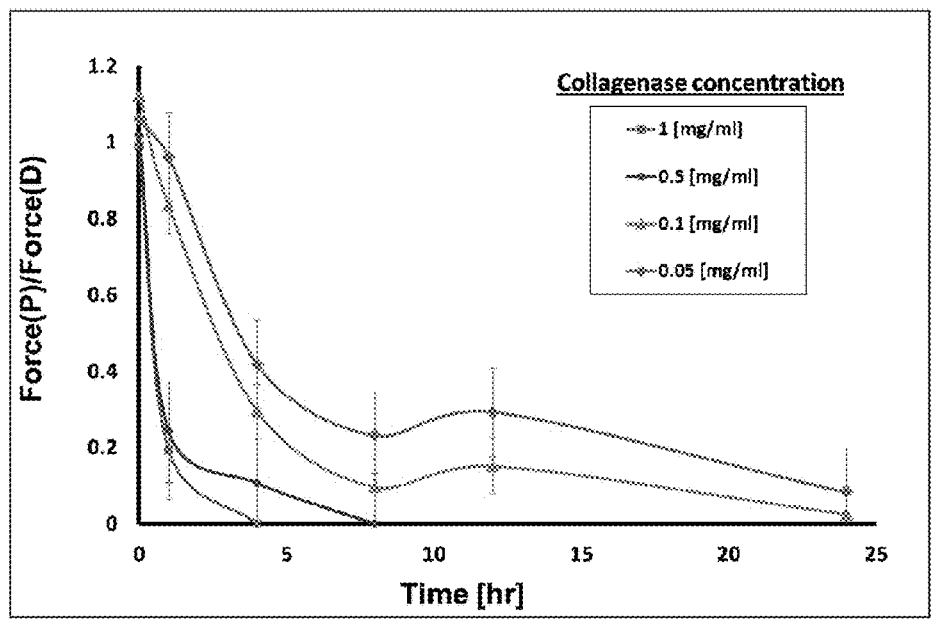
FIG. 4 is a graph showing collagenase relaxing effect on collagen fibers in a time- and concentration-dependent manner, the force (P) being the maximal force needed for tearing the proximal side of the fiber and force (D) being the maximal force needed for tearing the distal side of the fiber.

Collagen fibers were exposed to collagenase at different concentrations for different periods of time. As shown in FIG. 4, the increase in collagenase concentration and in treatment time resulted in weakening of the collagen fibers. At the high collagenase concentrations, i.e. 0.5 and 1 mg/mL, the collagen fibers tore within less than 10 hours. The ratio between force (P) and force (D) is defined as α where for untreated fibers α=1, for treated fibers 0≤α<1.

All presented data points are the mean of 5 experimental points±SD of the mean.

Example 1C: Collagen Fibers Relaxation Causes Fibroblasts Morphological Change The fibroblasts morphological change was recorded using confocal microscope Confocal Zeiss LSM 700 for 90 min. The cells were stained using Hoescht 33042 stock solution. Untreated bundle was placed on the confocal microscopy and 1 µl of 2 mg/ml collagenase solution was added to the bundle. A 90 sec interval confocal scan program scan took place in order to record the changes.

Figure 5A:
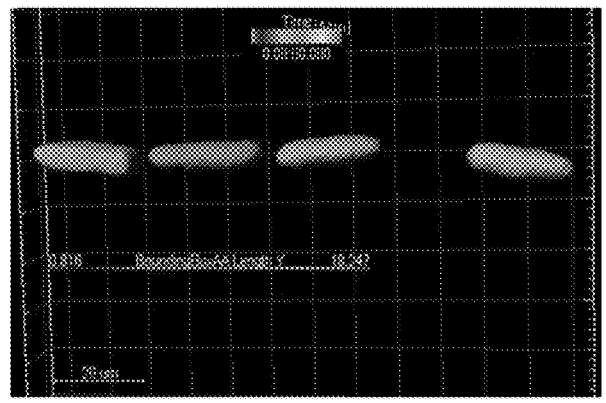
FIGS. 5A-5C are confocal scans of collagen fibers after treatment with collagenase type I at different time points following the treatment (FIG. 5A time=0, FIG. 5B T=33 min, FIG. 5C T=82 min).
Figure 5B:
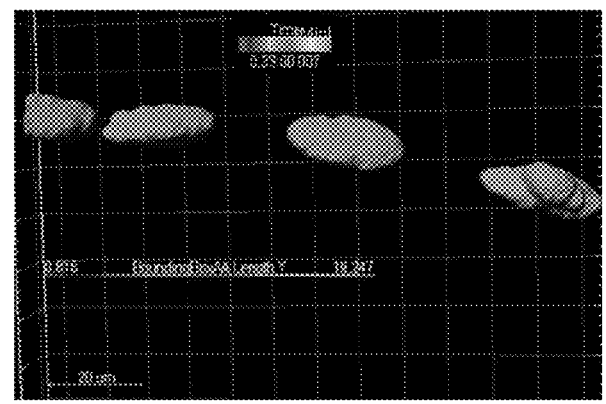
Figure 5C:
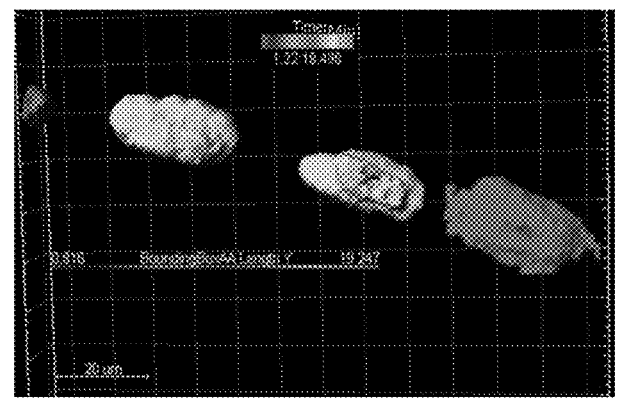

FIGS. 5A-5C show that collagenase treatment relaxed the collagen fibers, which assemble the bundle, thereby changed the formation of the fibroblasts attached to the bundle over time (FIG. 5A time=0, FIG. 5B T=33 min, FIG. 5C T=82 min).

Example 1D: The Morphological Effect of Collagenase on Collagen Fibers

Collagen fibers were immersed for 3.5 hours in a collagenase solution at a concentration of 1 mg/ml. In order to obtain high resolution scanning electron microscopy (Zeiss Ultra plus) samples, the bundles were placed on a stab containing carbon fiber tape and dried in a close sample box. The bundles were observed using the Everhart-Thornley secondary electron detector and the secondary electron 2 detector.

FIG. 6A shows a control collagen fiber where FIG. 6B shows that collagenase treatment disrupted the collagen fibers and thereby decreased its mechanical strength.

Example 2

Example 2A: Encapsulating Collagenase in Liposomes

Type I *Clostridium histolyticum* collagenase (Sigma-Aldrich) was encapsulated in liposomes (MLV) by dissolving 1,2-dimyristoyl-sn-glycero-3-phosphocholine (DMPC, Avanti Polar Lipids, Alabaster, Ala.) and cholesterol (Sigma-Aldrich, 70:30 mole ratio) in ethanol, and then injected the lipid mixture into phosphate buffered saline, containing 2 mg/ml collagenase type I to form multi-lamellar liposomes (average diameter of 5 micron). In order to create liposomes of 200 nm diameter from the MLV liposomes, the solution containing the liposomes was extruded using the extruder machine.

The liposomes were downsized by step-wise extrusion, using polycarbonate membranes (GE Osmonics), having pore diameters of 400 and 200 [nm] liposomes. Particle size was measured using dynamic light scattering (ZetaSizer ZSP, Malvern). As shown in FIG. 7, dynamic light scattering measurements indicated that the particle size, after loading with collagenase, was approx. 220 nm.

Example 2B: Release Profile of Collagenase from Liposomes

Collagenase encapsulated liposomes were synthesized as described above. The mixture was centrifuged for 10 min at 10,000 rpm at 4° C. The supernatant was removed and 10% PBS was added. The supernatant was kept separately. Then, all the tubes were vortexed and kept in the incubator at 37° C. with 5% humidity.

For each test time one tube was centrifuged at the same conditions described before. The supernatant sample that includes the released enzymes, was taken and absorbed using a protein measure kit.

Figure 8A:
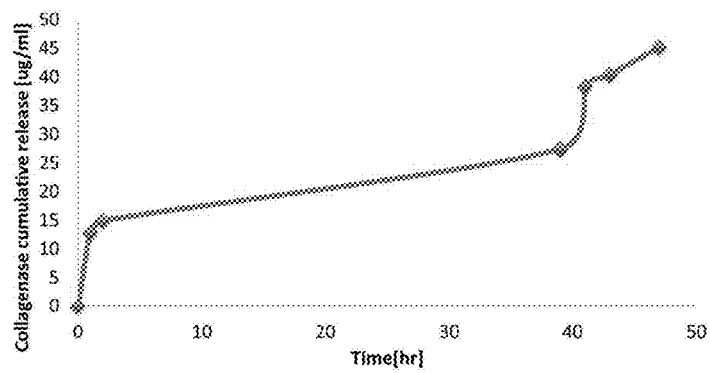
FIGS. 8A and 8B are graphs showing cumulative collagenase release from liposomes over time under burst conditions, with different cholesterol levels.

As shown in FIG. 8A, the enzyme was released from the liposome during time. In addition, the enzyme release was found to be related to the extra-liposomal concentration of the enzyme.

Figure 8B:
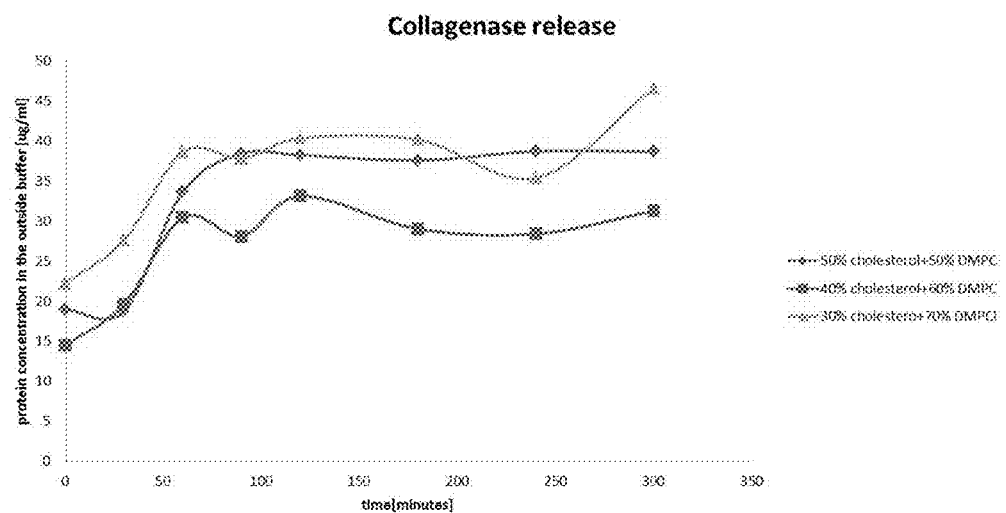

In a similar experiment, collagenase was encapsulated in liposomes with different cholesterol %, namely, 30%, or 40% or 50% and the released enzyme was measured. The results are shown in FIG. 8B. The figure shows that 40% cholesterol inhibited release of the enzyme as compared to 30% or 50%.

Example 2C: The Effect of Encapsulated Collagenase Compared with Free Enzyme Bundles of collagen type I (30 bundles) were extracted and cut in the middle. Collagenase type I (0.1 mg/ml) was encapsulated in 200 nm liposomes.

In addition, 2 ml of free collagenase 1 (0.1 mg/ml) were added to 30 tubes consist of 30 halves parts of the bundles and 2 ml of the encapsulated 0.1 mg/ml collagenase type I were added the second halves of the bundles. The influence of the encapsulation on the bundles relaxation was observed with respect to time.

Figure 9:
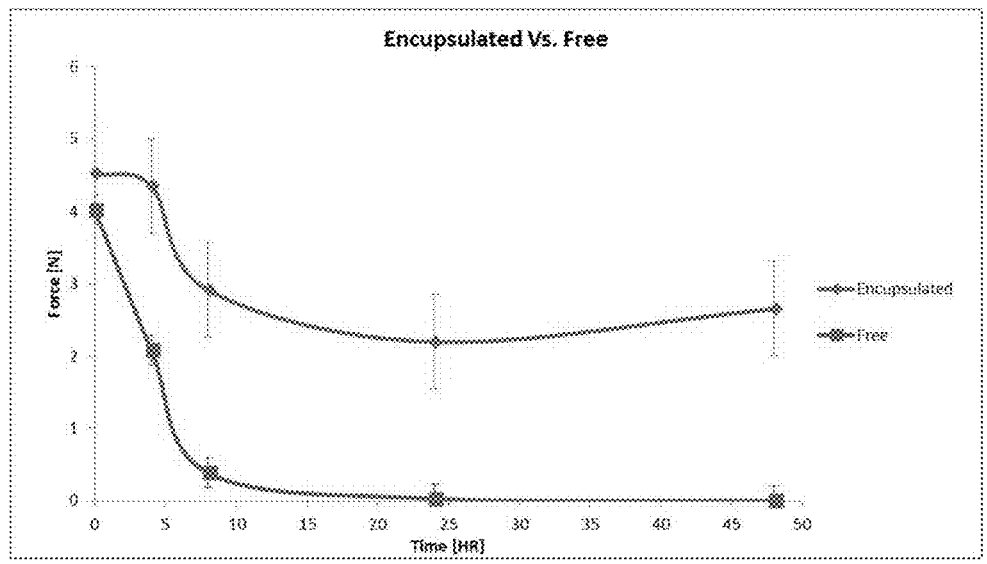
FIG. 9 is a graph showing the effect of free collagenase and encapsulated collagenase on collagen fibers.

In FIG. 9 the collagen fibers were cut in the middle, and exposed one part of the bundle to free collagenase, and the second part of the bundle to encapsulated collagenase. The concentrations of the collagenase were the same. As the treatment time increased, both parts of the fibers became mechanically weaker. While the collagen fibers exposed to the encapsulated collagenase only relaxed over time (the Force that is needed to apply in order to tear them decreased), the collagen fibers exposed to the free collagenase tore within less than 24 hours.

Example 3: Pre-Clinical Experiments

All animal trials were approved by the Technion Institutional Ethical Committee (IL-0380313). All animal studies follow strict guidelines as defined by the Max Plank Institutes.

The animal studies have a dual goal: the first goal is following the bio distribution of the nanoparticles in the animal body and specifically in the oral cavity. The second goal is to prove that the orthodontic treatment plus the enzymatic biosurgery procedure is more effective than orthodontic treatment by itself.

Efficacy Experiment

The purpose of this experiment was to evaluate the improvement in orthodontic movement of teeth using the liposomal formulation in the oral cavity.
The Study Model:

The study was conducted on rats as further detailed below.

A Ni—Ti coil is a 9 mm closed coil spring nickel and titanium alloy having 2 eyelets with an inner radius of 0.76 mm (3M UNITEK) was used. This type of coil has been used and studied in orthodontics for years and has proven to be affective in orthodontics procedures. The NiTi coil spring generates constant force when extended between 12-24 mm. The extension that was applied in the rat's mouths was in that range so that the force applied on the tooth would be the same on all the rats that participated in the experiment [J. A. von Fraunhofer, P. W. Bonds, B. E. Johnson, Force generation by orthodontic coil springs. *Angle Orthod* 63, 145-148 (1993); published online EpubSummer (10.1043/0003-3219 (1993)063<0145:fgbocs>2.0.co;2].

The tooth movement efficacy experiment was performed on male Wister rats in four different Studies. Three Studies consisted of 8 rats divided into two groups of 4 rats each, while the fourth Study consisted of 3 rats.

The First Study was aimed at comparing the movement of the left $1^{st}$ molar in the upper palate when using the collagenase encapsulated liposomes (unilamellar, 200 nm) versus Empty Liposomes, both installed with the Ni—Ti closed coil springs.

The Second Study was aimed at comparing the movement of the $1^{st}$ molar in the upper palate when using mixture of collagenase encapsulated multi-lamellar liposomes and Free Collagenase versus mechanical force of the Ni—Ti closed coil springs which is considered the common orthodontic procedure.

The Third Study was aimed at comparing the movement of the $1^{st}$ molar in the upper palate when using non encapsulated collagenase (free) treatment versus the common orthodontic procedure—i.e. mechanical force of the Ni—Ti closed coil springs.

The Fourth Study was aimed at examining the movement of the $1^{st}$ molar in the upper palate while administering a mixture of collagenase encapsulated multi-lamellar liposomes and free enzyme to the rats every 3 days in order to simulate a controlled release therapeutic dose, as opposed to the earlier three Studies in which the enzyme was administered only on the $1^{st}$ day for simulating bulk injection.

The general state of the rats was monitored by weighing them every 3-4 days to account for weight fluctuations.

All rats were anesthetized in two stages. At first, the rats were anesthetized using isoflurane. Secondly, each rat was injected intramuscular to the biceps femoris with a mixture of Ketamine and Xylazine.

The liposomes were injected in PBS.

After each treatment, the rats were transferred and kept in a 29° C. incubator, with constant oxygen flow, until they reached full recovery (full alertness).

Collagenase concentration of 2 mg/ml was used this concentration for the 200 nm liposomes. MLV, free enzyme in order to compare between the different studies.

For the $1^{st}$, $2^{nd}$ and $3^{rd}$ Studies the agent (liposomal collagenase, free collagenase or empty liposomes) were injected on each side of the $1^{st}$ upper molar before installing the Ni—Ti coil device. In the $4^{th}$ Study the liposomal collagenase was injected on each side of the $1^{st}$ upper molar at three time points after which measurement was taken.

The procedure of installing the Ni—Ti coil was performed using human orthodontics equipment and materials. Specifically, the $1^{st}$ upper molar and the upper incisors were dried and cleaned using cotton swabs to remove any debris that accumulated. The teeth were conditioned, using Transbond Plus™ etching primer conditioning agent (3M UNITEK), for 5-10 seconds creating a rugged surface, hence allowing stronger bonding of the Ni—Ti coil. Following conditioning, a small amount of composite Transbond™ LR light cure adhesive (3M UNITEK), was spread over the molar and the eyelet ring of the Ni—Ti coil was placed in parallel with the tooth and light cured using LEDEX™ dental curing light for 10-15 seconds. Once again, a small amount of the bonding agent was spread over the ring and light cured for at least 40 seconds. The binding of the incisors was performed in a similar manner. Cleaning, drying and conditioning of the incisors were initially done.

Figures 10A, 10B:
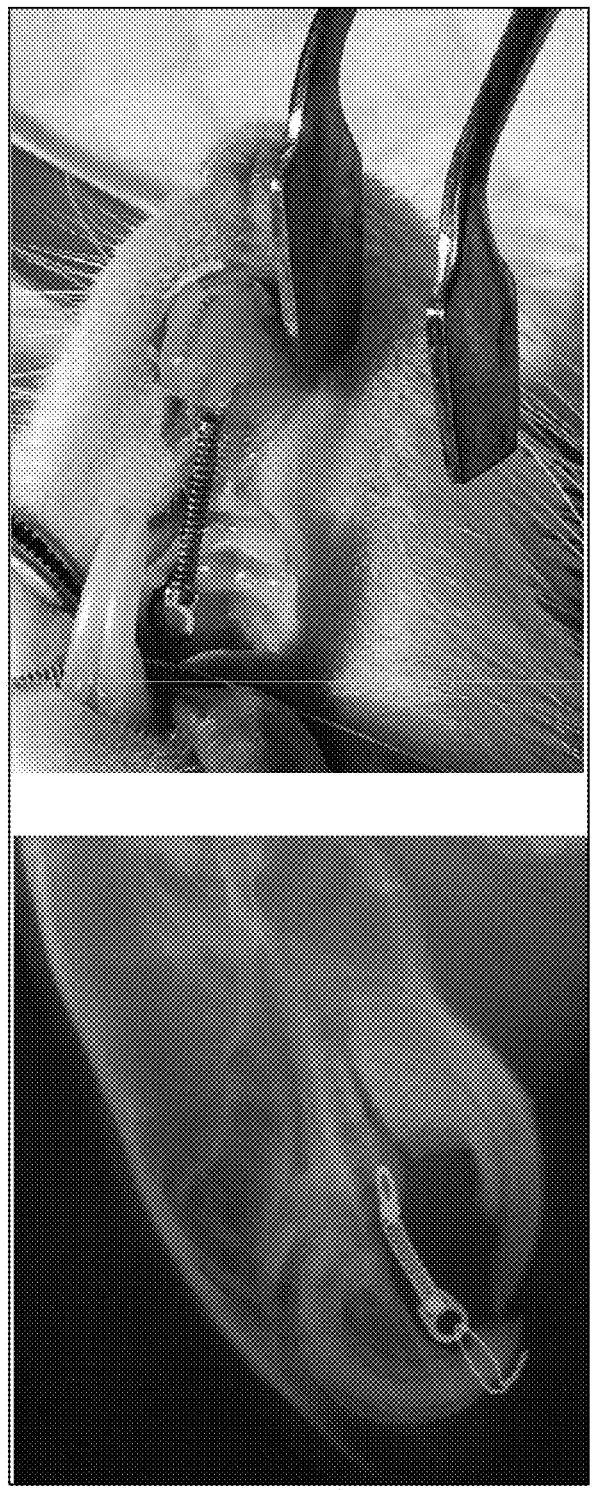
FIG. 10A-10B are images showing the placement of the Ni—Ti coil spring around the front upper incisors and 1$^{st}$ right maxillary molar of the rat, FIG. 10A showing 2D head X-ray view, and FIG. 10B showing live rat in this animal model undergoing tooth movement procedure.

Subsequently, a stainless ligature was placed through the second eyelet ring of the Ni—Ti coil and by braiding it around the incisors it was possible to achieve strong binding (FIG. 10B).

Measurements were taken every 3 to 4 days (up to 15 days total) using a digital caliper with an instrument error of 0.02 mm. the measurements included distance between the eyelet of the Ni—Ti coil on the $1^{st}$ molar and the back of the upper incisors. For every measurement, the rats were weighed and then anesthetized using isoflurane (isoflurane allowed fast measurements and short recovery time for the rats).

The influence, with respect to time, of the tested agent (liposomal collagenase, free collagenase or empty liposomes) was observed and compared to no biosurgery treatment.

FIG. 10A-10B show the placement of the Ni—Ti coil around the front upper incisors and 1st left molar of the rat. (10A) Dental X-ray view, (10B) Live animal view. Gap between the moving mesial molar and the stationary distal molar can be seen in the animal view (FIG. 10A).

Figure 11:
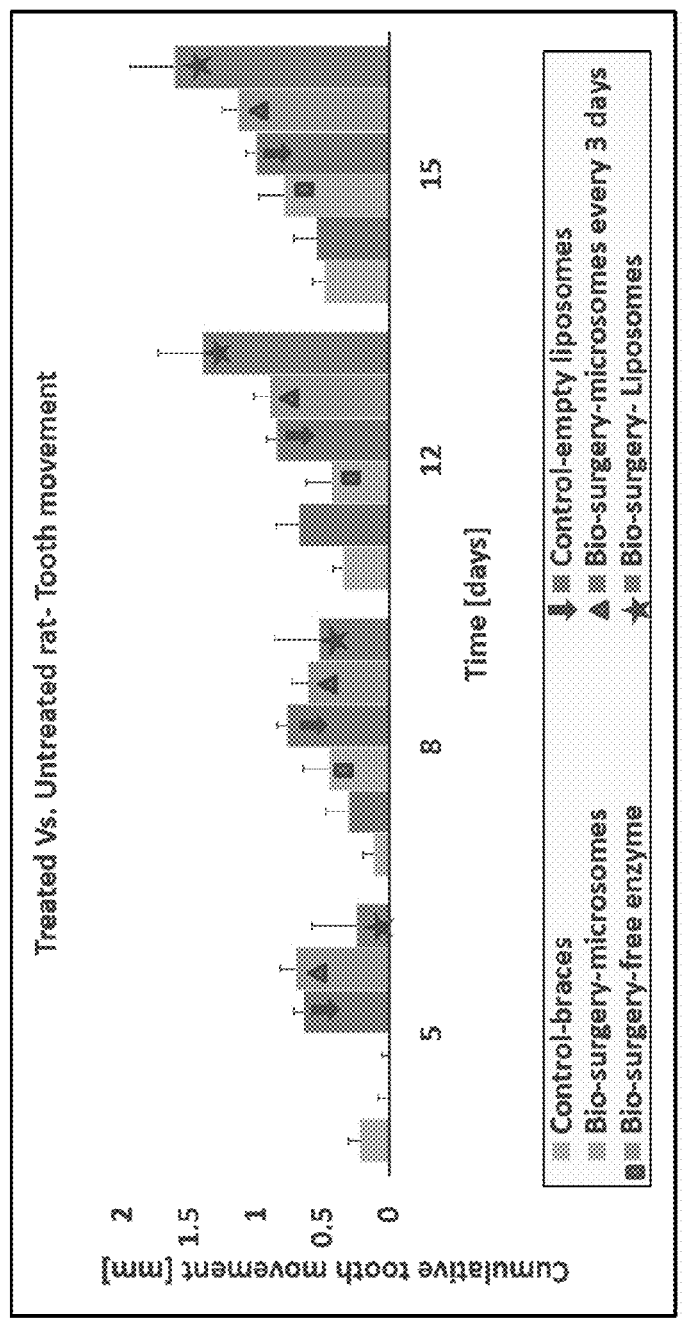
FIG. 11 is a bar graph showing the cumulative tooth movement during a 15 day study on the effect of liposomal collagenase vs. free collagenase, empty liposomes and control (braces) group.

Further, the results of this Experiment are presented in FIG. 11 shows the Cumulated tooth movement during 15 days. In all stages of the experiment, with the bars being from left to right, in each indicated day (5, 10, 12 or 15)

control braces (the most left bar), empty liposomes, microliposomes/microsomes encapsulating collagenase, the microsomes delivered every three days, free enzyme (collagenase), liposomes encapsulating collagenase (most right lane).

Specifically, the molar tooth of the group treated with liposomal collagenase shifted an average a distance of ~1.7 mm in the 15 days period of the experiment. This is opposed to the teeth movement of the control group where only braces were used to move the teeth, which showed an average cumulated tooth movement of ~0.49 mm (~71% less than the liposomal collagenase treated group).

Empty liposomes showed an average cumulated tooth movement of ~0.63 mm (~63% less than the liposomal collagenase treated group).

Free collagenase had an average cumulated tooth movement of ~1.13 mm (~33% less than the liposomal collagenase treated group).

When comparing multi-lamellar liposomes with unilamellar liposomes, it was observed that despite excessive tooth movements from both liposomal groups, the unilamellar liposome group achieves a larger cumulated tooth movement, probably due to its larger size.

Figure 12:
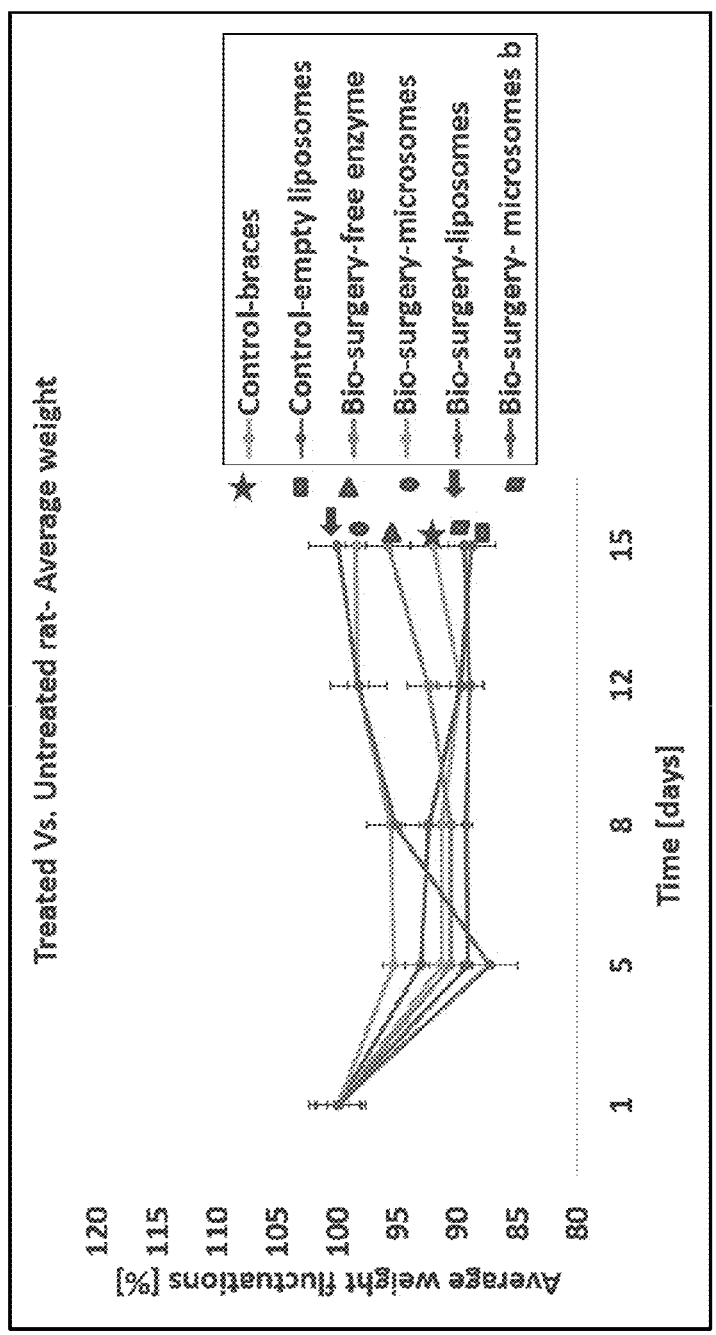
FIG. 12 is a graph showing animals' weight fluctuation during treatment.

During the study, the rats' weight was monitored. FIG. 12 presents the average weight fluctuations (%), and shows that all study groups had a weight loss during the first 5 days of the experiment. From the $5^{th}$ day, all rats gained weight.

Bio-Distribution Experiments

The purpose is to study the distribution of the liposomal collagenase in the oral cavity. For this purpose, the experiment was performed on male Wistar rats using the CRI Maestro in-vivo imaging machine calibrated to the following parameters: system wavelength: 780-820, exposure: 5000, excitation filter-690 [nm], emission filter-750 nm.

ICG (Crio-Green) was encapsulated in multi-lamellar liposomes by dissolving 1,2-dimyristoyl-sn-glycero-3-phosphocholine (DMPC, Avanti Polar Lipids, Alabaster, Ala.) and cholesterol (Sigma-Aldrich, 70:30 mole ratio) in ethanol, followed by injection of the lipid mixture into phosphate buffered saline, containing 1.8 mg/ml ICG, to form florescence multi-lamellar liposomes. The solution of florescence multi-lamellar liposomes was dialyzed with PBS overnight in order to separate the encapsulated ICG from the non-encapsulated one.

The florescence multi-lamellar liposomes were simultaneous injected to 5 male Wistar rats on each side of the $1^{st}$ upper molar, the same injection sites used for the efficacy experiment, 10 µl each side.

The total length of the experiment was 24 hours, in which measurements were taken in the following hour's gap times: 0, 1, 4, 8, 12, 24. For every measurement, the rat was dissected and it organs (upper jaw, tongue, heart, lungs, spleen, liver, kidneys) were testes using the CRI Maestro in-vivo imaging machine. The results intensity values were normalized to the highest signal in all organs. Values under 0.5% of the highest value were neglected.

In addition, tissues that are not subjected to histological studies were homogenized in order to quantify the amount of the fluorescent marker.

Figure 13:
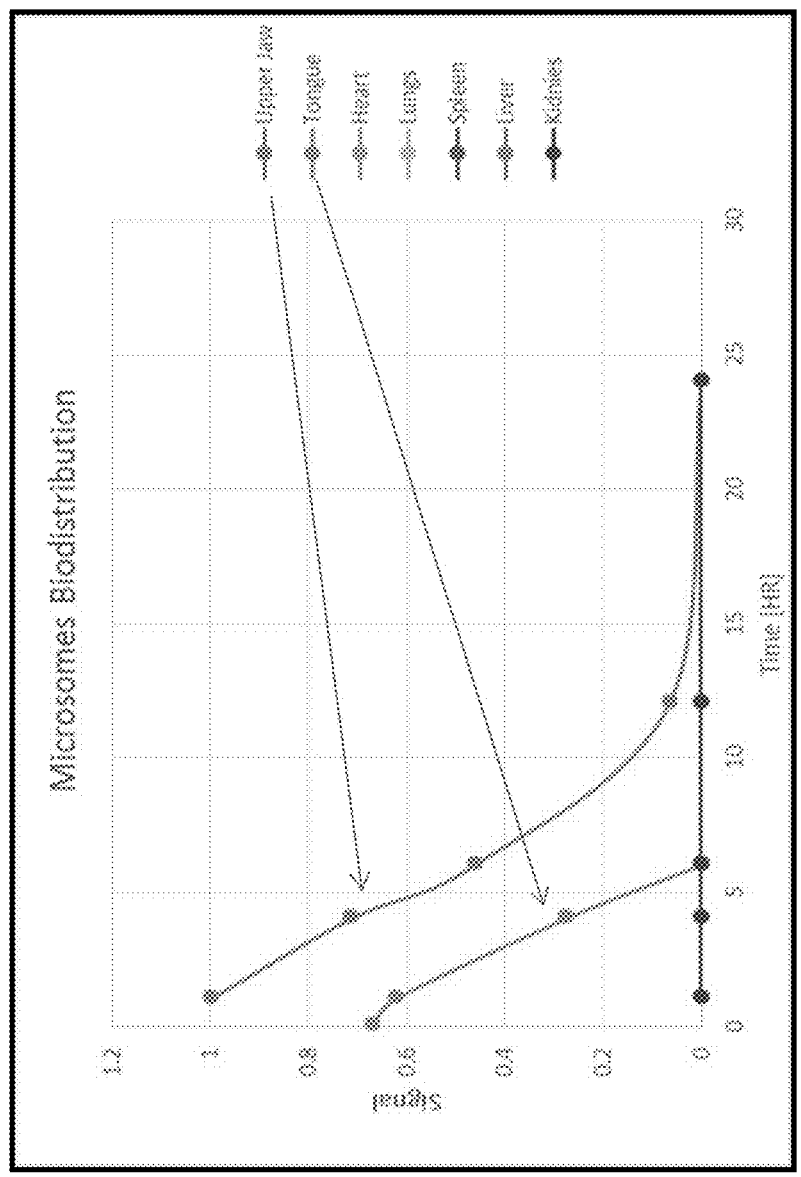
FIG. 13 is a graph showing the liposomal collagenase biodistribution in time.

FIG. 13 presents signal intensity in the different tested organs. Specifically, as shown, the highest signal was found at the upper jaw, being the injected area. Liposomes roaming phenomenon was not observed in the other tested organs, except for the tongue. After 4 hours a significant decrease in the intensity signal was observed and the liposomes were completely evacuated from the body after approximately 12 hours.

Regeneration Evaluation

The regeneration of mechanical strength of the collagen fiber was tested with respect to time and following the addition of collagenase inhibitor, (EDTA).

As previously, collagen fibers were sourced from tails of Wistar rats. Each bundle was cut in half, a first half was used as an internal control and the other half used for tested treatment.

Figure 14B:
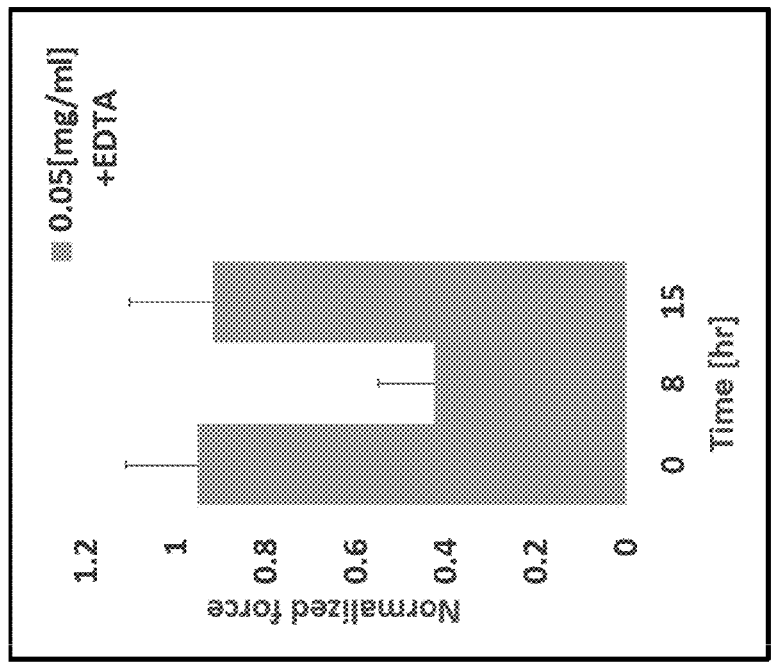
FIGS. 14A-14B are graphs showing the effect of collagenase on fiber relaxation without EDTA (collagenase inhibition, FIG. 14A) and after exposing to EDTA (FIG. 14B)
Figure 14A:
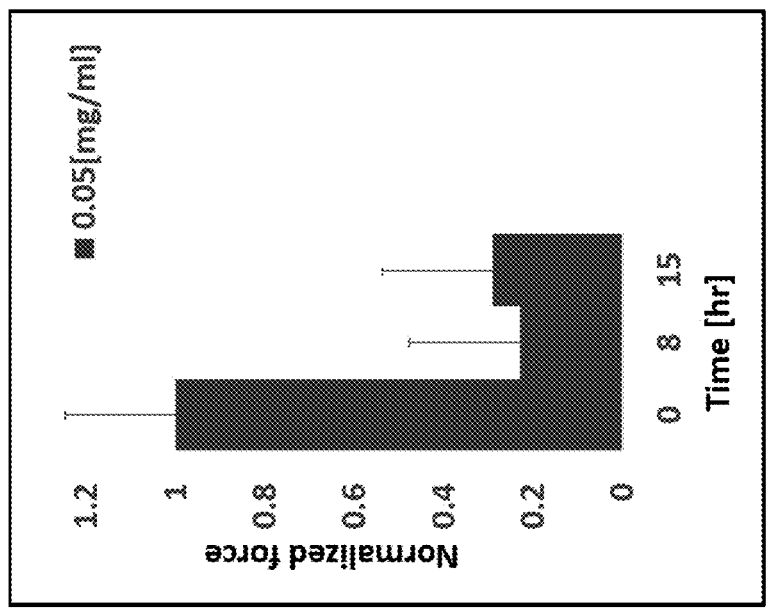

Collagen fibers were exposed to free collagenase at concentration of 0.05 mg/ml, for 8 hours in order to weaken the bundles. After 8 hours a concentration of 0.02M EDTA (Ethylenediaminetetraacetic acid) was added for 15 min in order to inhibit the enzyme activity and allow bundle regeneration. Subsequently, the media was removed and the treated bundles were washed twice with new growth media. The results are presented in FIG. 14A-14B showing collagen bundle relaxation in time without inhibiting collagenase activity (FIG. 14A) and effect of the inhibitor in allowing regeneration (FIG. 14B). All data points in the Figure are the mean of 14-20 experimental points. The results show that upon inhibition of collagenase activity the bundles regenerated about 90% of their initial strength.

Morphology

Figures 15A, 15B, 15C:
FIGS. 15A-15C are scanning electron microscope images of collagen bundle (FIG. 15A), after treatment with collagenase (FIG. 15B) and after cessation of collagenase effect by exposure to EDTA (FIG. 15C).

The morphological effect of free collagenase and collagenase inhibition on collagen fibers was also examined using a high resolution scanning electron microscopy (SEM Zeiss Ultra plus). To this end, SEM samples were prepared by placing the bundles on a carbon fiber stab tape and dried in a close sample box. The bundles were observed by the Everhart-Thornley secondary electron detector and the secondary electron 2 detector. The results are presented in FIGS. 15A-15C showing that the collagenase treatment led to collagen fiber detachment and assembly into bundles (FIG. 15B), thereby decreasing the mechanical force needed to tare the bundle and the fiber regeneration after treatment with EDTA (FIG. 15C). FIG. 15A presents the collagen fibers without treatment.

Histology

Histological sections (H&E) were made on liposomal collagenase treated Wistar rat jaw. After 15 days of treatment as described above, the close Ni—Ti coil spring was removed, followed by 19 days of recovery at which point, histology analysis took place. Specifically, the jaw was removed using scalpel and was kept on 10% formaldehyde solution until the H&E process. Following surgical removal by scalpel of the rat jaw, the specimens were formalin-fixed and paraffin-embedded. Serial sections (4 um in thickness) were routinely processed for hematoxylin and eosin staining.

Figure 16:
FIG. 16 is a histology section after 15 days of biosurgery treatment and 19 days of recovery.

FIG. 16 shows that the periodontal ligament (PDL) mesial (anterior) to the moving root was thinner and compressed compared to the thicker and tensed PDL sections in the opposite direction. Supracrestal fibers architecture post treatment was reserved.

Micro CT Scans

Micro CT scans were performed on liposomal collagenase treated Wistar rat using a high resolution in-vivo x-ray microtomograph system (SKYCA). To this end, the rat was scanned after 15 days, of treatment, removal of the close Ni—Ti coil and then followed by 19 days of recovery.

Figure 17A:
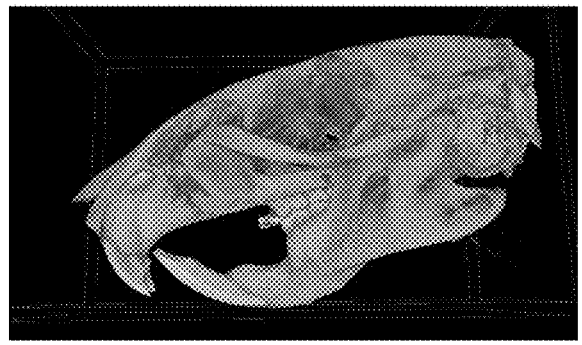
FIG. 17A-17C are micro CT images of buccal view of untreated upper left jaw (FIG. 17A) and liposomal collagenase treated upper right Jaw (FIG. 17B) and axial cut of treated rat (FIG. 17C).
Figure 17B:
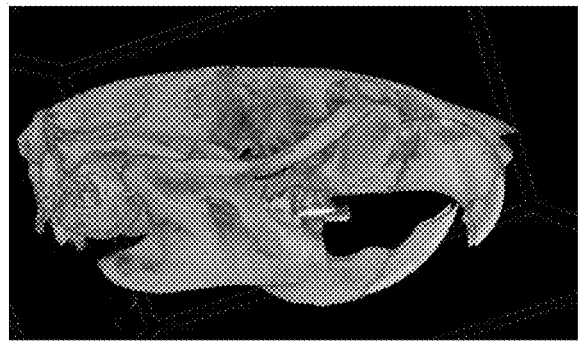
Figure 17C:

FIGS. 17A-17C show that axial cut of the treated rat where lower alveolar bone density (calculate it using CT) can be noticed and calculated surrounding the treated area, the first upper right molar (C) compare to the control, untreated first upper left molar. Integrating the CT scans and from the histology results it is assumed that the bone organic scaffold still exists, although the mineral was transiently resorbed, making this osteopenia effect—reversible.

Further, alveolar bone resorption can be notice between the first and the second molars due to the orthodontic movement of the tooth. Lower alveolar bone density surrounding the treated area can be noticed and calculated, the first upper right molar (FIG. 17C) compare to the control, untreated first upper left molar. Integrating the CT scans and the histology results allows to assume that the bone organic scaffold still exists, although the mineral is transiently resorbed, making this osteopenia effect-reversible.

Example F: Pilot Experiment

The purpose is to study if extraction of two bilateral teeth is possible. Measurements of teeth movement is accurate if the comparison is made in the same animal, namely to an opposite teeth that is not treated. Thus, two opposite teeth are extracted in the mandible.

In order to verify that there is no effect on the extraction, in four rats—two teeth are extracted and in four rats only one tooth is extracted. This provides monitoring the animal behavior—weight, movement and general appearance in each one of the groups. Each group includes eight rats.

The results are informative as to the possibility to extract two teeth in a rat.

The invention claimed is:

1. A delivery system comprising:
   (i) a physiologically acceptable carrier, and
   (ii) a liposome formulation encapsulating a proteolytic enzyme or an effector thereof, wherein the proteolytic enzyme or effector thereof has absolute specificity to said proteolytic enzyme's target,
   wherein said proteolytic enzyme is selected from collagenase and an enzyme with absolute specificity to Type I collagen, and
   wherein the concentration of said proteolytic enzyme or effector thereof is equal to or less than 1 mg/mL.

2. The delivery system of claim 1, wherein the delivery system is for relaxing fibers within an oral cavity of the subject, optionally fibers between a tooth's alveolar bone and gingival.

3. The delivery system of claim 1, for use in relaxing fibers within a target connective tissue.

4. The delivery system of claim 1, wherein said liposomes are unilamellar or multi-lamellar liposomes.

5. The delivery system of claim 1, wherein said liposomes comprise at least one liposome forming lipid and cholesterol.

6. The delivery system of claim 5, wherein said liposomes comprise a mole ratio between said at least one liposome forming lipid and cholesterol of between 50:50 to 95:5.

7. The delivery system of claim 5, wherein said liposomes comprise a mole ratio between said at least one liposome forming lipid and cholesterol of about 70:30.

8. The delivery system of claim 1, wherein the liposomes are embedded in a polymeric matrix.

9. The delivery system of claim 8, wherein the polymeric matrix comprises a cross-linked polymer.

10. The delivery system of claim 1, wherein the delivery system is for teeth repositioning or for orthodontic teeth alignment.

11. The delivery system of claim 4, wherein said multi-lamellar liposomes have an average diameter of 400-200 nm.

12. The delivery system of claim 1, wherein the proteolytic enzyme effector is a proteolytic enzyme precursor.

13. The delivery system of claim 2, wherein at least fibers between the tooth's alveolar bone and gingival are relaxed without causing complete rupture of the connective tissue surrounding the tooth.

14. The delivery system of claim 2, wherein at least fibers between the tooth's alveolar bone and gingival are relaxed while maintaining integrity of the fibers surrounding the tooth.

15. The delivery system of claim 1, wherein said absolute specificity to a target comprises neglectable or no detectable catalytic activity to any other fiber.

16. The delivery system of claim 1, wherein said proteolytic enzyme has absolute specificity to Type I collagen.

17. The delivery system of claim 1, wherein said liposome formulation encapsulates only said proteolytic enzyme or an effector thereof.

18. A method for causing relaxation of fibers within a subject's connective tissue, the method comprises administering the delivery system of claim 1 to the subject.

19. A method for tooth repositioning, comprising:
   administering a delivery system comprising a physiologically acceptable carrier and a liposome formulation encapsulating a proteolytic enzyme or effector thereof to said subject's periodontal pocket, wherein said proteolytic enzyme is selected from collagenase and an enzyme with absolute specificity to Type I collagen, and wherein said proteolytic enzyme or effector thereof has absolute specificity to said proteolytic enzyme's target and is at a concentration equal to or less than 1 mg/mL and effective to cause relaxation of fibers between a tooth's alveolar bone and gingival, and repositioning said tooth while said fibers are in a relaxed state.

* * * * *